(12) United States Patent
Balaganesan et al.

(10) Patent No.: US 10,014,480 B2
(45) Date of Patent: Jul. 3, 2018

(54) HETEROCYCLIC COMPOUNDS AND ORGANIC ELECTROLUMINESCENT DEVICES USING THE SAME

(71) Applicant: E-RAY OPTOELECTRONICS TECHONOLOGY CO., LTD., Chung-Li (TW)

(72) Inventors: Banumathy Balaganesan, Chung-Li (TW); Heh-Lung Huang, Chung-Li (TW); Cheng-Chung Yao, Chung-Li (TW); Po-Wei Hsieh, Chung-Li (TW); Hui-Hsu Chen, Chung-Li (TW)

(73) Assignee: E-RAY OPTOELECTRONICS TECHNOLOGY CO., LTD., Chung-Li (TW)

( * ) Notice: Subject to any disclaimer, the term of this patent is extended or adjusted under 35 U.S.C. 154(b) by 551 days.

(21) Appl. No.: 14/538,969

(22) Filed: Nov. 12, 2014

(65) Prior Publication Data
US 2016/0133848 A1    May 12, 2016

(51) Int. Cl.
*H01L 51/00* (2006.01)
*C07D 307/91* (2006.01)
(Continued)

(52) U.S. Cl.
CPC ........ *H01L 51/0073* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

| | | | | |
|---|---|---|---|---|
| 2009/0066235 A1* | 3/2009 | Yabunouchi | ......... | C07D 209/86 313/504 |
| 2014/0197386 A1* | 7/2014 | Kim | .................... | H01L 51/0067 257/40 |
| 2015/0280136 A1* | 10/2015 | Ryu | ........................ | C09K 11/06 257/40 |

FOREIGN PATENT DOCUMENTS

| JP | 2013-258022 | 12/2013 |
|---|---|---|
| JP | 2014-028774 | 2/2014 |

(Continued)

OTHER PUBLICATIONS

Machine English translation of JP 2013-258022 A. Sep. 15, 2017.*
(Continued)

*Primary Examiner* — J. L. Yang
(74) *Attorney, Agent, or Firm* — Amin, Turocy & Watson LLP

(57) ABSTRACT

The present invention discloses a novel heterocyclic compound of Formula (1) and an organic electroluminescent device using the same, in which variables are as described herein. The heterocyclic compound of Formula (1) is present in the emitting layer as a light emitting host in combination with a dopant and another host, in the organic electroluminescent device and high luminous efficiency and low driving voltage are achieved.

Formula (1)

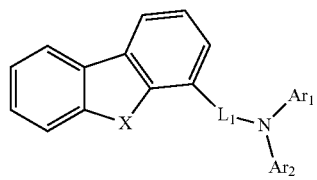

10 Claims, 7 Drawing Sheets

(51) Int. Cl.
*C07D 409/04* (2006.01)
*C07D 333/76* (2006.01)
*H01L 51/50* (2006.01)

(52) U.S. Cl.
CPC .......... *C07D 409/04* (2013.01); *H01L 51/006* (2013.01); *H01L 51/0059* (2013.01); *H01L 51/0072* (2013.01); *H01L 51/0074* (2013.01); *H01L 51/0085* (2013.01); *H01L 51/5016* (2013.01); *H01L 2251/5384* (2013.01)

(56) References Cited

FOREIGN PATENT DOCUMENTS

| | | |
|---|---|---|
| JP | 2014-116595 | 6/2014 |
| JP | 2015-131806 | 7/2015 |
| JP | 2016-086127 | 5/2016 |
| JP | 2016-092297 | 5/2016 |
| WO | 2014/067614 | 5/2014 |
| WO | 2014/097866 | 6/2014 |

OTHER PUBLICATIONS

Machine English translation of JP 2014-028774 A. Sep. 15, 2017.*
Japanese Office Action for Japanese Patent Application No. 2015-218382 dated Jan. 4, 2017.
Japanese Office Action for Japanese Patent Application No. 2015-218382 dated Apr. 17, 2017.

* cited by examiner

HETEROCYCLIC COMPOUNDS AND ORGANIC ELECTROLUMINESCENT DEVICES USING THE SAME

BACKGROUND OF THE INVENTION

Field of the Invention

This invention relates generally to heterocyclic compounds for organic electroluminescent devices. The invention further relates to heterocyclic compounds containing dibenzothiophene or dibenzofuran molecular structure in the core skeleton and phosphorescent organic electroluminescent devices using the same.

Description of Related Art

Recently, organic electroluminescent devices (OLED) are considered to be emissive display technology competitive to other display technologies such as liquid crystal displays (LCDs) and light emitting diodes (LEDs). OLED devices are commercially attractive because they offer the cost-advantageous fabrication of high density pixeled displays exhibiting brilliant luminance, high efficiency, low driving voltage, with true color and longer operational stability.

A typical OLED comprises at least one emitting layer sandwiched between an anode and a cathode. When a current is applied, the anode injects holes and the cathode injects electrons into the organic layer(s). The injected holes and electrons each migrate toward the oppositely charged electrode. When an electron and hole localize on the same molecule, an "exciton", which is a localized electron-hole pair having an excited energy state, is formed. Light is emitted when the exciton relaxes through a photoemissive mechanism. To improve the charge transport capabilities and also the luminous efficiency of such devices, additional layers around the emitting layer, such as an electron transport layer and/or a hole transport layer, or an electron blocking and/or hole blocking layer(s) have been incorporated. Doping the host material with another material (guest) has been well demonstrated in literature to enhance the device performance and to tune the chromaticity. Several OLED materials and device configurations are described in U.S. Pat. Nos. 4,769,292, 5,844,363, and 5,707,745, which are incorporated herein by reference in their entirety.

More recently, OLEDs having emissive materials that emit light from triplet states (phosphorescence) have been demonstrated in literature, Nature, 1998, No. 395, p. 151 and Appl. Phys. Lett., 1999, No. 3, p. 4, and U.S. Pat. No. 7,279,704, which are incorporated herein by reference in their entirety.

Selection of a host material in phosphorescent OLEDs is difficult especially since the non-emissive triplet excited state of the host material must be higher than that of the guest phosphor (dopant). In addition, a host material must have good charge transport properties for an efficient OLED. JP2001-313178 disclosed CBP (4,4'-bis(N-carbazolyl)-1,1'-biphenyl) as the host material, which is characterized by having a good hole transport property but poor electron transporting. Hence the use of CBP as a host material for tris(2-phenylpyridine) iridium (hereinafter referred to as Ir(ppy)3), a green phosphorescent emitter, disturbs balanced injection of electrical charges, causing excess holes to flow towards the electron transport layer, thereby decreasing the luminous efficiency. Moreover, due to its low molecular weight, it tends to crystallize and thus is not suitable for OLED devices.

One of the means to solve the above problem is to introduce a hole blocking layer between the emitting layer and the electron transport layer as described in JP2002-305083. This hole blocking layer accumulates holes efficiently in the emitting layer and contributes to increase the probability of recombination of holes and electrons and thus enhances the luminous efficiency. Currently, the hole-blocking materials in general use include 2,9-dimethyl-4,7-diphenyl-1,10-phenanthroline (hereinafter referred to as BCP) and phenylphenolato-bis(2-methyl-8-quinolinator-N1,08)aluminum (hereinafter referred to as BAlq). However, BCP tends to crystallize even at room temperature and lacks reliability as a hole blocking material and the life of the device is extremely short; whereas BAlq has insufficient hole blocking ability.

For a high luminous and efficient OLEDs, a host material must have non-emissive high triplet energy and a balanced electrical charge (hole/electron) injection/transport characteristics. Moreover, the host material should also possess good electrochemical stability, high thermal resistance and excellent thin film stability. However, compound capable of satisfying all the said properties from practical considerations have not been known till date.

Attempts have been made to introduce molecular moiety that has an excellent hole transport property as represented by a carbazole or triarylamine and another moiety that has an excellent electron transport property as represented by pyrimidine or triazine into one and the same molecular skeleton, as phosphorescent host materials, as disclosed in the patent documents WO2003-78451, WO2005-76668, US2006-51616, JP2008-280330, WO2008-123189 and JP 2009-21336.

Dibenzothiophenes (DBT) and dibenzofuran (DBF) are some of the heterocyclic moieties having a high triplet energy and a high mobility, which does not shown to have intense absorptions in the visible region. Its co-planarity is quite favorable for intermolecular interaction. Patent documents U.S. Pat. No. 8,007,927, KR20110085784, U.S. Pat. No. 8,409,729 and US20140151649 disclose the use of benzodithiophenes or dibenzofurans used in the light emitting devices.

However, it still needs a desired OLED having characteristics in terms of high luminance, operational stability and reduced driving voltage.

SUMMARY OF THE INVENTION

In order to achieve the aforesaid, the present invention provides heterocyclic compounds containing dibenzothiophene or dibenzofuran molecular structure in the core skeleton and an OLED comprising the heterocyclic compounds.

The heterocyclic compounds of the present invention is represented by the following Formula (1):

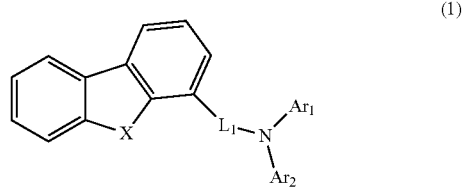

wherein
X represents a heteroatom;
$L_1$ represents a $C_6$-$C_{30}$arylene;
$Ar_1$ represents a substituted or unsubstituted $C_6$-$C_{15}$aryl; and $Ar_2$ represents a substituted or unsubstituted $C_6$-$C_{15}$aryl; or $Ar_2$, N and $L_1$ are taken together to form a substituted or unsubstituted carbazole moiety, wherein at least one of $Ar_1$ and $Ar_2$ possesses an aromatic hydrocarbon moiety having 10 to 15 atoms by allowing each of $Ar_1$ and $Ar_2$ to be substituted with from 0 to 3 substituents independently selected from the group consisting of $C_1$-$C_{30}$alkyl, $C_6$-$C_9$aryl and di-($C_6$-$C_9$)arylamino. The OLED of the present invention comprises a substrate; an anode formed on the substrate; a cathode; and at least one emitting layer formed between the anode and the cathode, wherein the emitting layer includes a phosphorescent dopant and the heterocyclic compound of the present invention as host material.

According to the invention, the heterocyclic compound of Formula (1) is present in the emitting layer as a light emitting host. For example, the heterocyclic compound of Formula (1) can be in combination with a dopant and another host, in the organic electroluminescent device such that high luminous efficiency and sufficient low driving voltage are achieved.

DETAILED DESCRIPTION OF THE PREFERRED EMBODIMENTS

Figure 1:
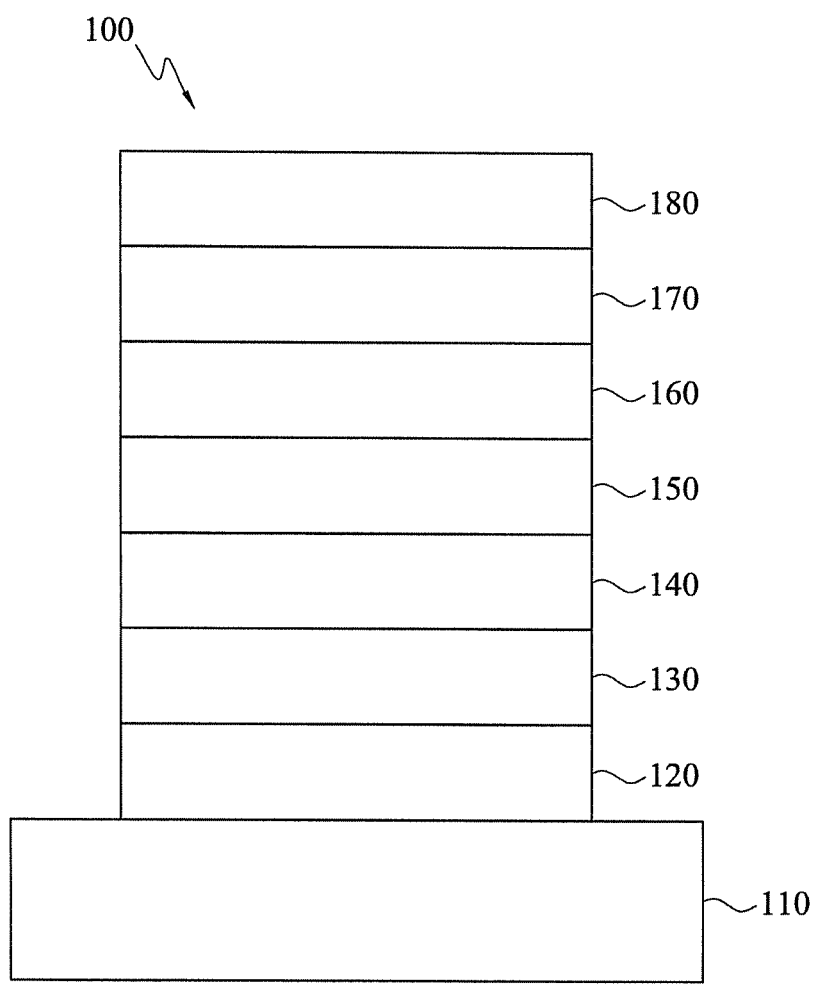
FIG. 1 is a cross-sectional view illustrating one example of an organic electroluminescent according to an embodiment of the present invention.

The detailed description of the present invention is illustrated by the following specific examples. Persons skilled in the art can conceive the other advantages and effects of the present invention based on the disclosure contained in the specification of the present invention.

The heterocyclic compound of the present invention is represented by the following Formula (1):

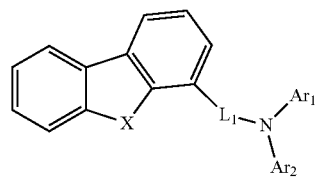

(1)

wherein

X represents a heteroatom;

$L_1$ represents a $C_6$-$C_{30}$arylene;

$Ar_1$ represents a substituted or unsubstituted $C_6$-$C_{15}$aryl; and $Ar_2$ represents a substituted or unsubstituted $C_6$-$C_{15}$aryl; or $Ar_2$, N and $L_1$ are taken together to form a substituted or unsubstituted carbazole moiety, wherein at least one of $Ar_1$ and $Ar_2$ possesses an aromatic hydrocarbon moiety having 10 to 15 atoms by allowing each of $Ar_1$ and $Ar_2$ to be substituted with from 0 to 3 substituents independently selected from the group consisting of $C_1$-$C_{30}$alkyl, $C_6$-$C_9$aryl and di-($C_6$-$C_9$)arylamino.

In one embodiment, the carbazole moiety is 2,9-carbazolylene or 3,9-carbazolylene.

In one embodiment, the carbazole moiety is substituted with $C_6$-$C_{15}$aryl. Preferably, in the above heterocyclic compound, the carbazole moiety is substituted with phenyl, naphthyl or biphenyl.

In one embodiment, in the above heterocyclic compound, $Ar_1$ and $Ar_2$ are each independently substituted or not.

In further embodiment, $Ar_1$ and $Ar_2$ are each independently substituted with $C_1$-$C_{30}$alkyl, $C_6$-$C_9$aryl or di-($C_6$-$C_9$)arylamino, preferably substituted with dimethyl, phenyl or diphenylamino.

The substituent may be linked through any position of the substituent. For example, the diphenylamino is linked to the phenyl through para-position. However, the diarylamine is not linked to the phenyl group through the ortho-position.

In one embodiment of the above heterocyclic compound, $Ar_1$ and $Ar_2$ each independently represent phenyl, naphthyl, biphenyl, dimethylfluorenyl or triphenylamino.

In one embodiment, X represents S or O; $L_1$ represents phenylene; and $Ar_1$ and $Ar_2$ each independently represent phenyl, naphthyl, biphenyl, dimethylfluorenyl or triphenylamino.

In one embodiment, X represents S or O; $Ar_1$ represents phenyl, naphthyl, biphenyl, dimethylfluorenyl or triphenylamino; and $Ar_2$, N and $L_1$ are taken together to form a substituted or unsubstituted carbazole moiety. Preferable examples of the heterocyclic compounds represented by the aforementioned Formula (1) are shown below, but not limited to.

Compound 1-1

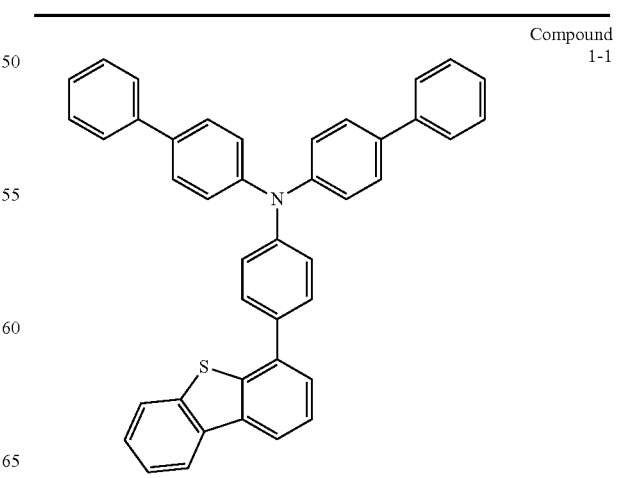

Compound 1-2
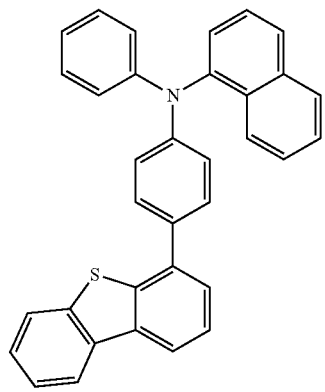
Compound 1-3
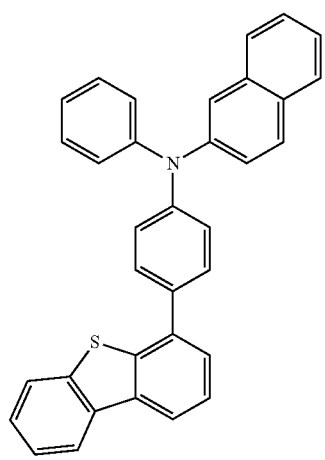 [SMILES: c1ccc(N(c2ccc(-c3cccc4c3sc3ccccc34)cc2)c2ccc3ccccc3c2)cc1]
Compound 1-4
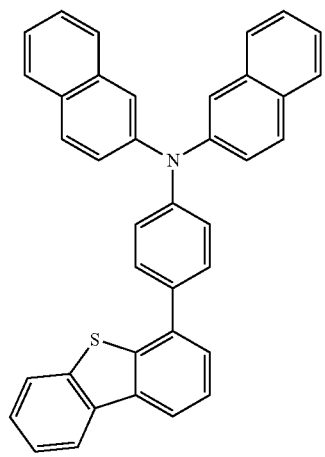 [SMILES: c1ccc2cc(N(c3ccc(-c4cccc5c4sc4ccccc45)cc3)c3ccc4ccccc4c3)ccc2c1]
Compound 1-5
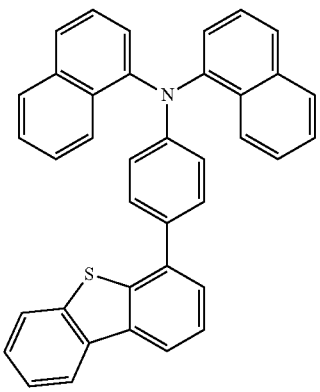
Compound 1-6
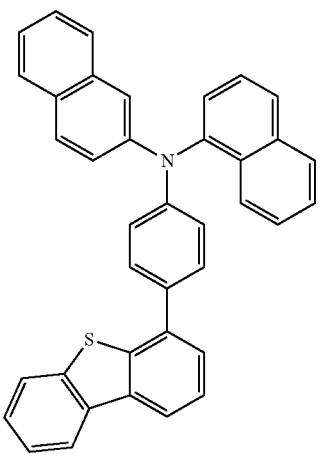
Compound 1-7
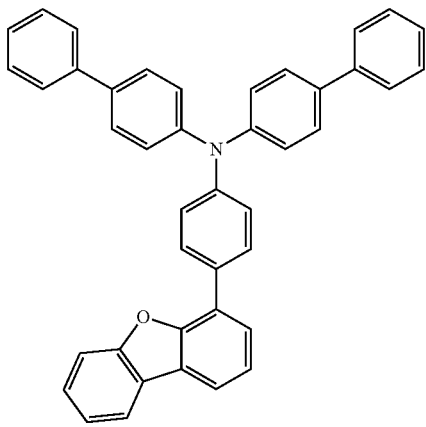

Compound 1-8
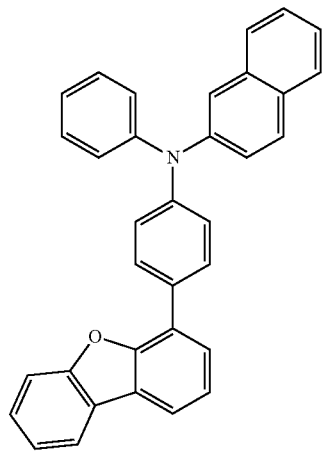 [SMILES: c1ccc(N(c2ccc(-c3cccc4c3oc3ccccc34)cc2)c2ccc3ccccc3c2)cc1]
Compound 1-9
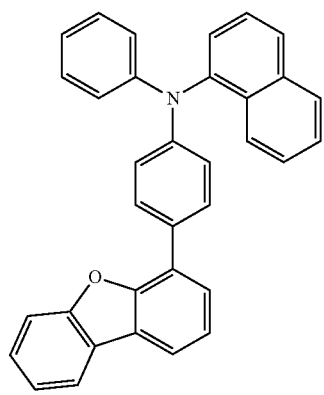 [SMILES: c1ccc(N(c2ccc(-c3cccc4c3oc3ccccc34)cc2)c2cccc3ccccc23)cc1]
Compound 1-10
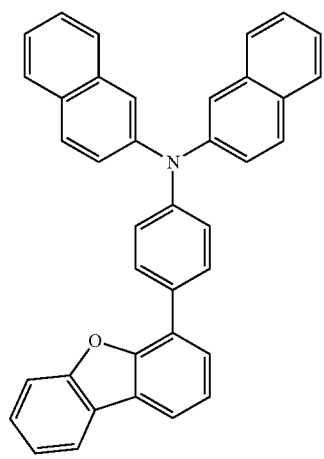 [SMILES: c1ccc2cc(N(c3ccc(-c4cccc5c4oc4ccccc45)cc3)c3ccc4ccccc4c3)ccc2c1]
Compound 1-11
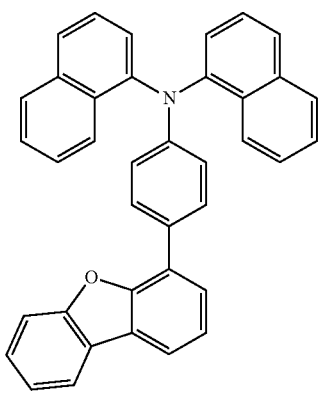 [SMILES: c1ccc2c(N(c3ccc(-c4cccc5c4oc4ccccc45)cc3)c3cccc4ccccc34)cccc2c1]
Compound 1-12
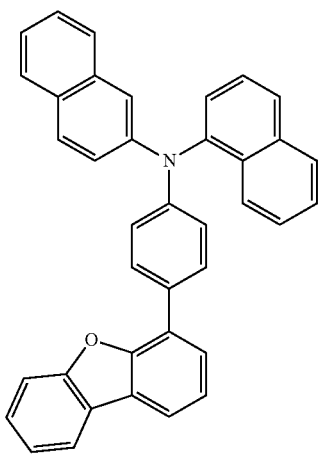 [SMILES: c1ccc2cc(N(c3ccc(-c4cccc5c4oc4ccccc45)cc3)c3cccc4ccccc34)ccc2c1]
Compound 1-13
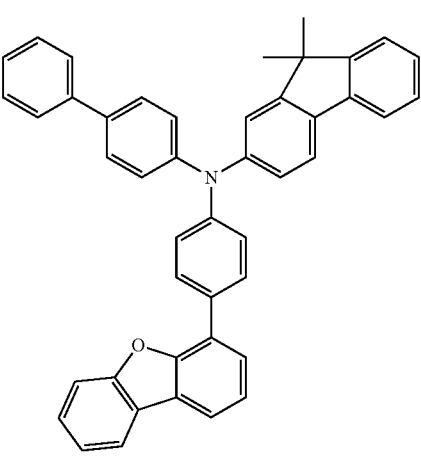 [SMILES: CC1(C)c2ccccc2-c2ccc(N(c3ccc(-c4ccccc4)cc3)c3ccc(-c4cccc5c4oc4ccccc45)cc3)cc21]

Compound 1-14
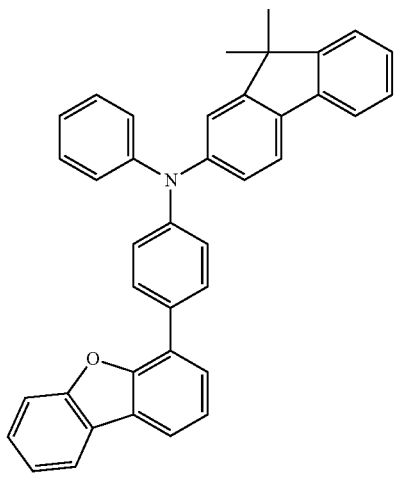 [SMILES: CC1(C)c2ccccc2-c2ccc(N(c3ccccc3)c3ccc(-c4cccc5c4oc4ccccc45)cc3)cc21]
Compound 1-15
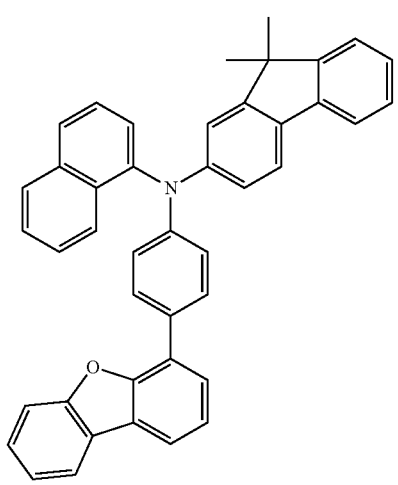 [SMILES: CC1(C)c2ccccc2-c2ccc(N(c3ccc(-c4cccc5c4oc4ccccc45)cc3)c3cccc4ccccc34)cc21]
Compound 1-16
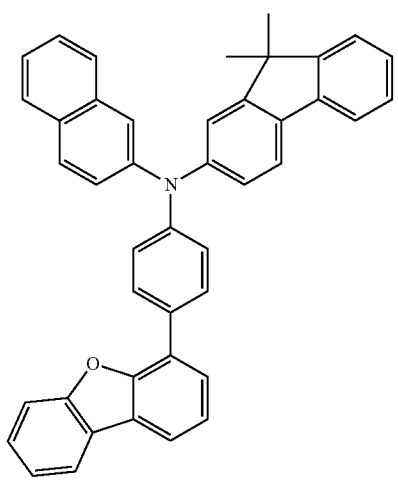 [SMILES: CC1(C)c2ccccc2-c2ccc(N(c3ccc(-c4cccc5c4oc4ccccc45)cc3)c3ccc4ccccc4c3)cc21]
Compound 1-17
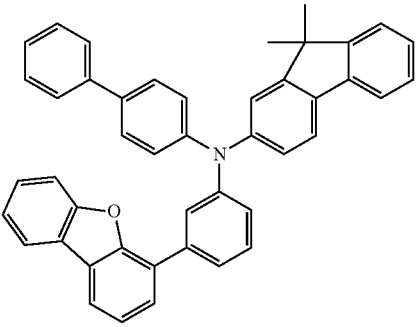 [SMILES: CC1(C)c2ccccc2-c2ccc(N(c3ccc(-c4ccccc4)cc3)c3cccc(-c4cccc5c4oc4ccccc45)c3)cc21]
Compound 1-18
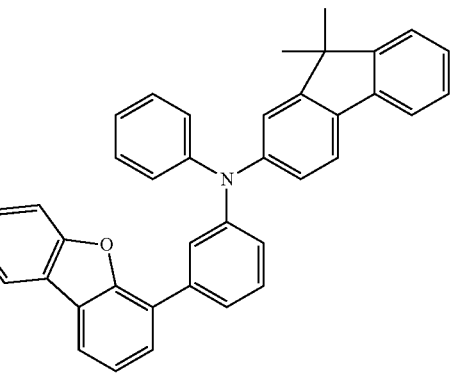
Compound 1-19
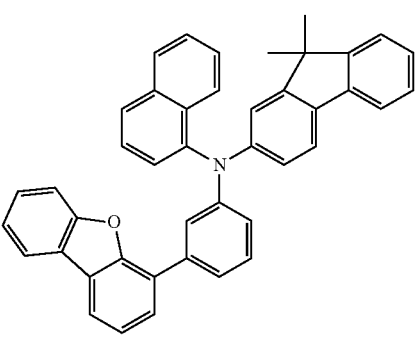 [SMILES: CC1(C)c2ccccc2-c2ccc(N(c3cccc(-c4cccc5c4oc4ccccc45)c3)c3cccc4ccccc34)cc21]
Compound 1-20
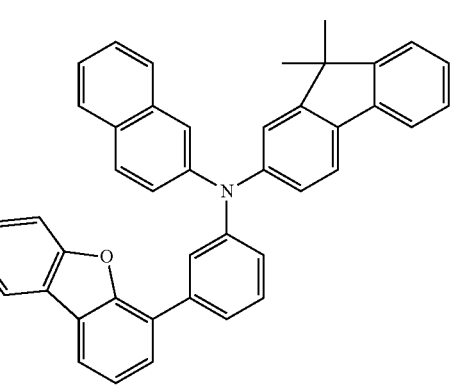

Compound 1-21
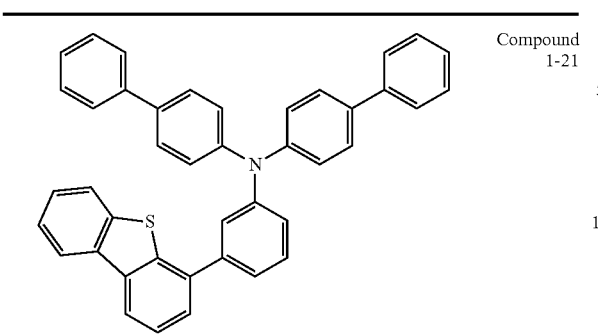
Compound 1-22
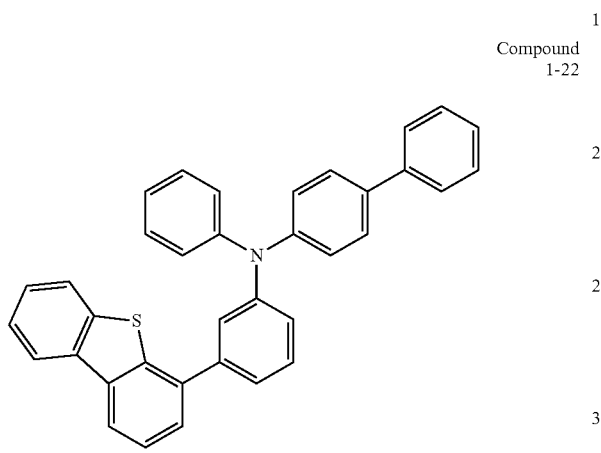
Compound 1-23
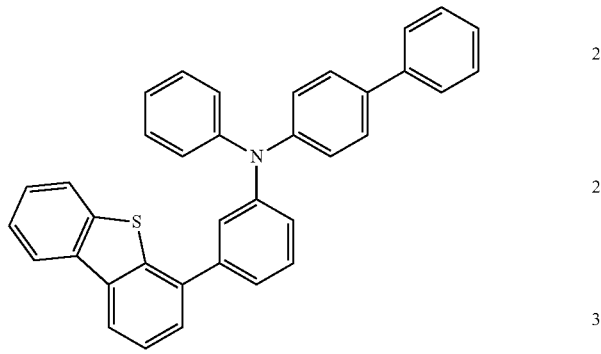
Compound 1-24
Compound 1-25
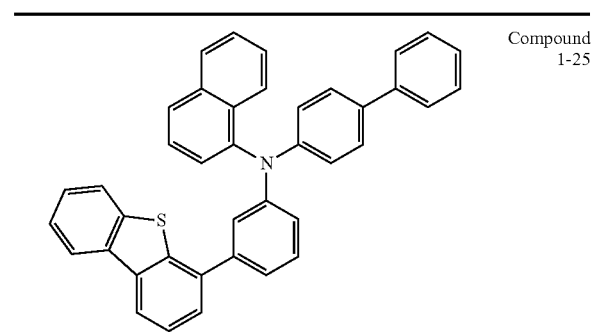
Compound 1-26
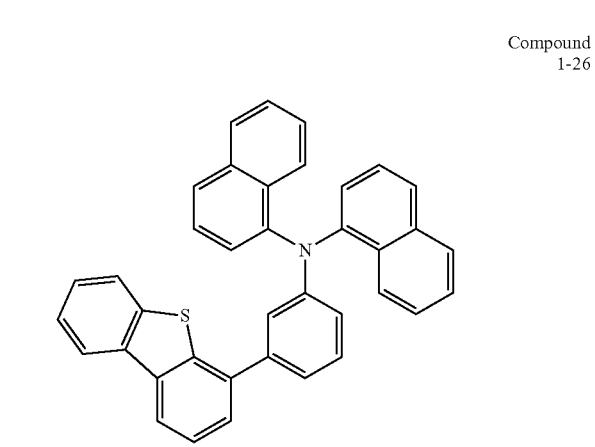
Compound 1-27
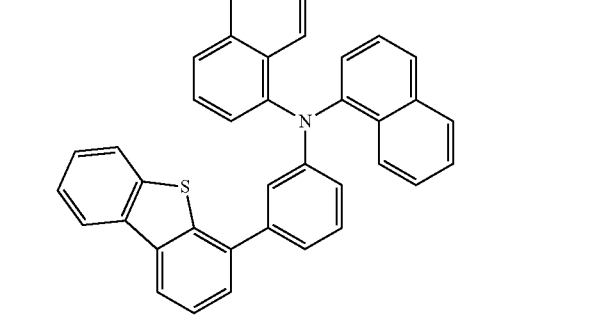
Compound 1-28

Compound 1-29
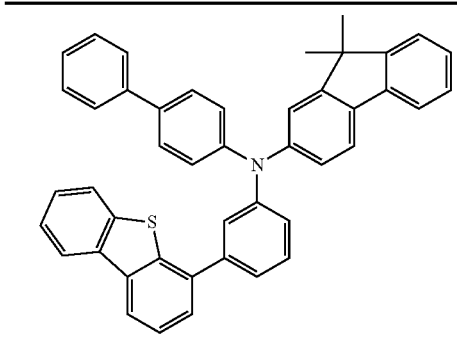
Compound 1-30
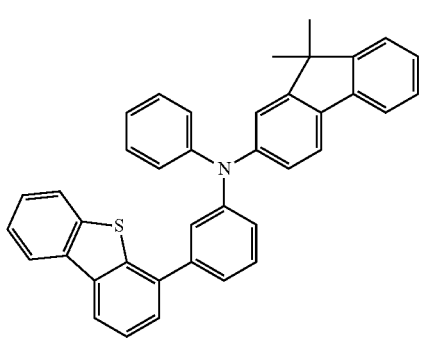 [SMILES: CC1(C)c2ccccc2-c2ccc(N(c3ccccc3)c3cccc(-c4cccc5c4sc4ccccc45)c3)cc21]
Compound 1-31
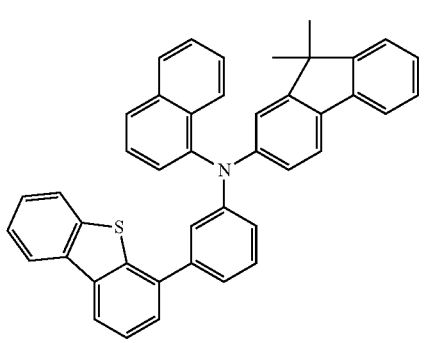 [SMILES: CC1(C)c2ccccc2-c2ccc(N(c3cccc(-c4cccc5c4sc4ccccc45)c3)c3cccc4ccccc34)cc21]
Compound 1-32
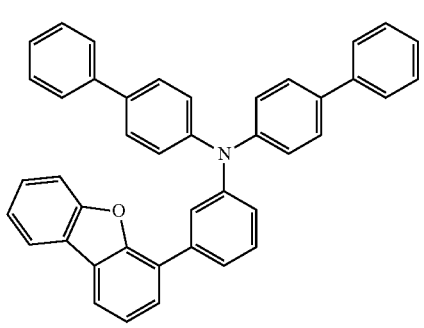 [SMILES: c1ccc(-c2ccc(N(c3ccc(-c4ccccc4)cc3)c3cccc(-c4cccc5c4oc4ccccc45)c3)cc2)cc1]
Compound 1-33
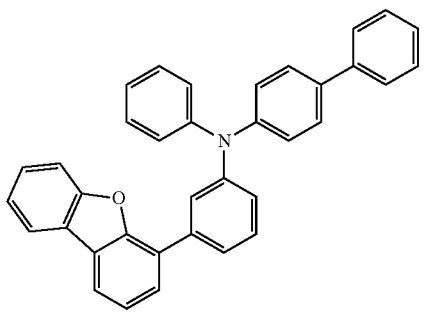 [SMILES: c1ccc(-c2ccc(N(c3ccccc3)c3cccc(-c4cccc5c4oc4ccccc45)c3)cc2)cc1]
Compound 1-34
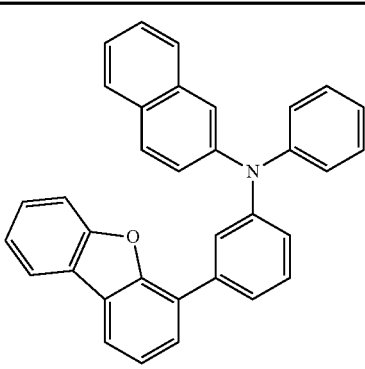
Compound 1-35
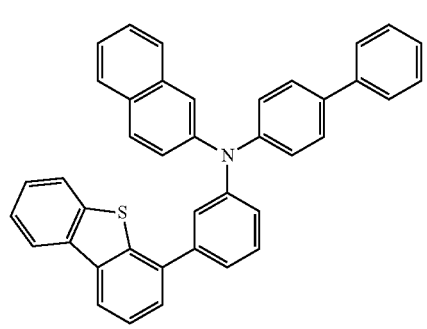 [SMILES: c1ccc(-c2ccc(N(c3cccc(-c4cccc5c4sc4ccccc45)c3)c3ccc4ccccc4c3)cc2)cc1]
Compound 1-36
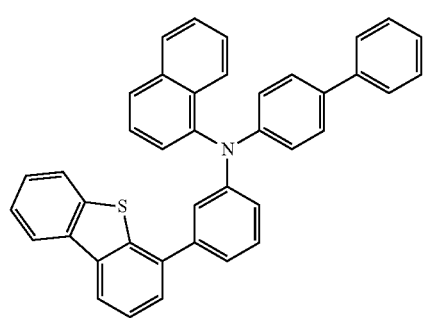 [SMILES: c1ccc(-c2ccc(N(c3cccc(-c4cccc5c4sc4ccccc45)c3)c3cccc4ccccc34)cc2)cc1]
Compound 1-37
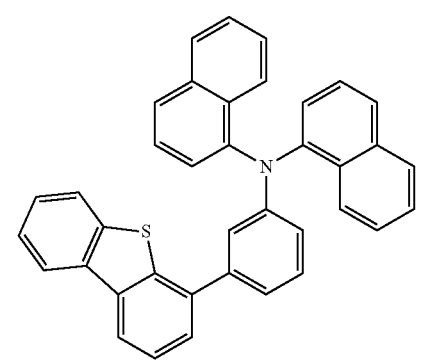 [SMILES: c1cc(-c2cccc3c2sc2ccccc23)cc(N(c2cccc3ccccc23)c2cccc3ccccc23)c1]

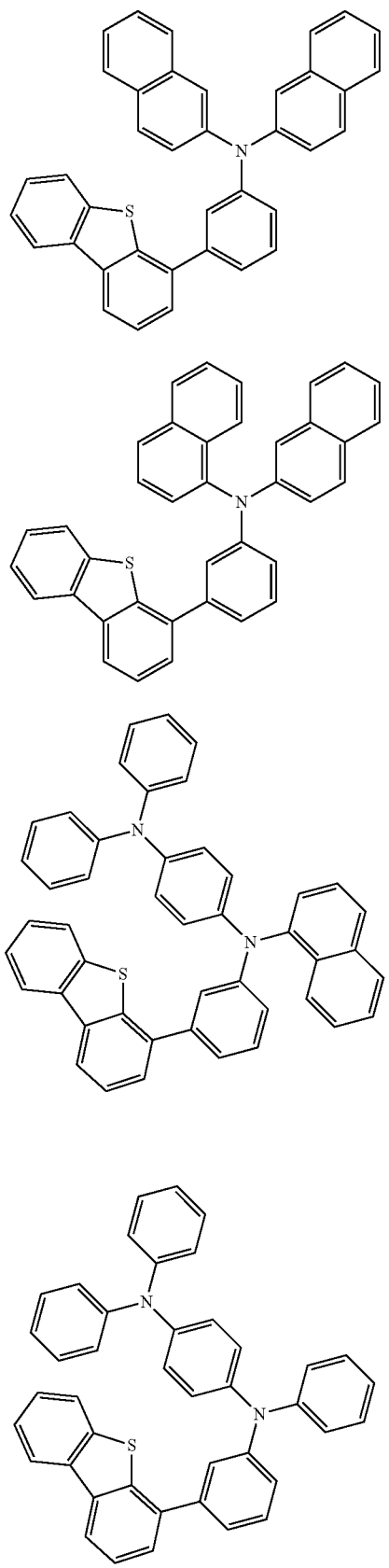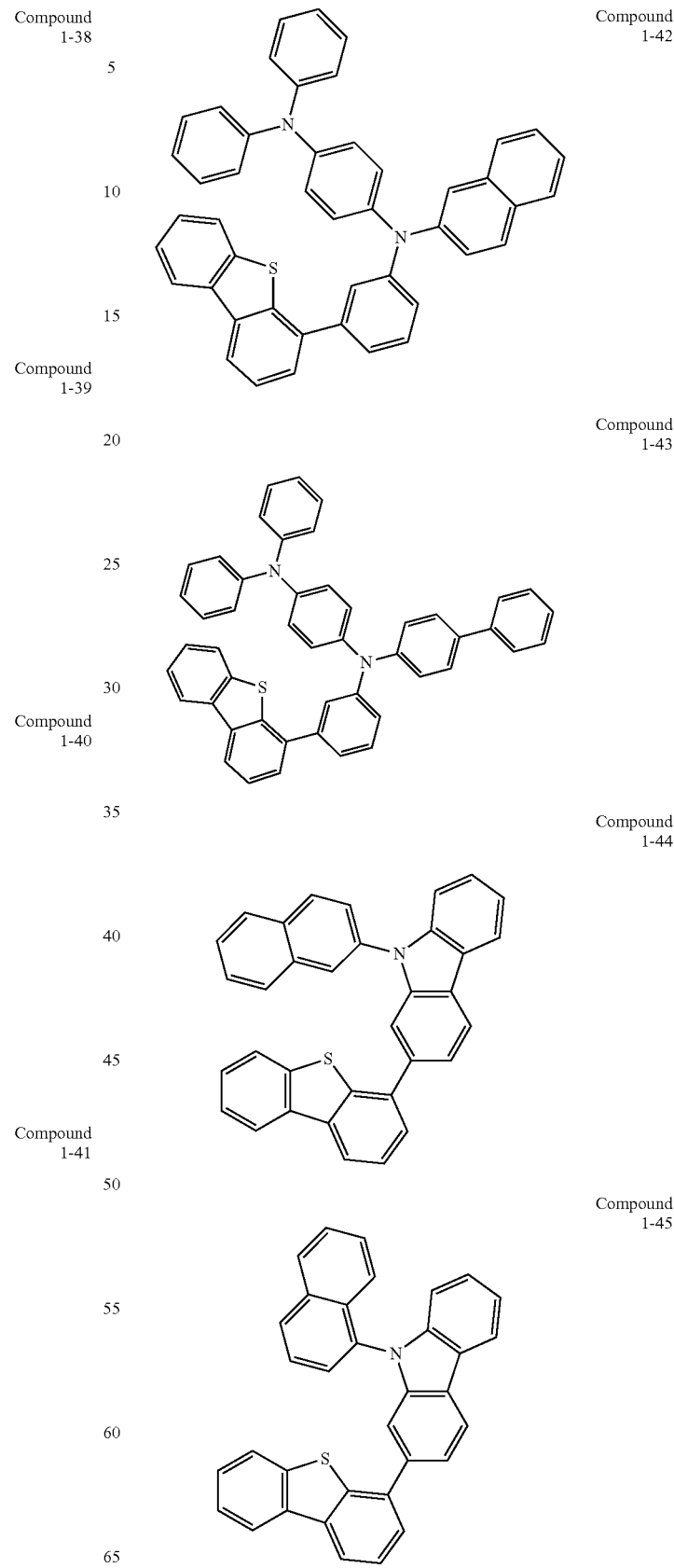

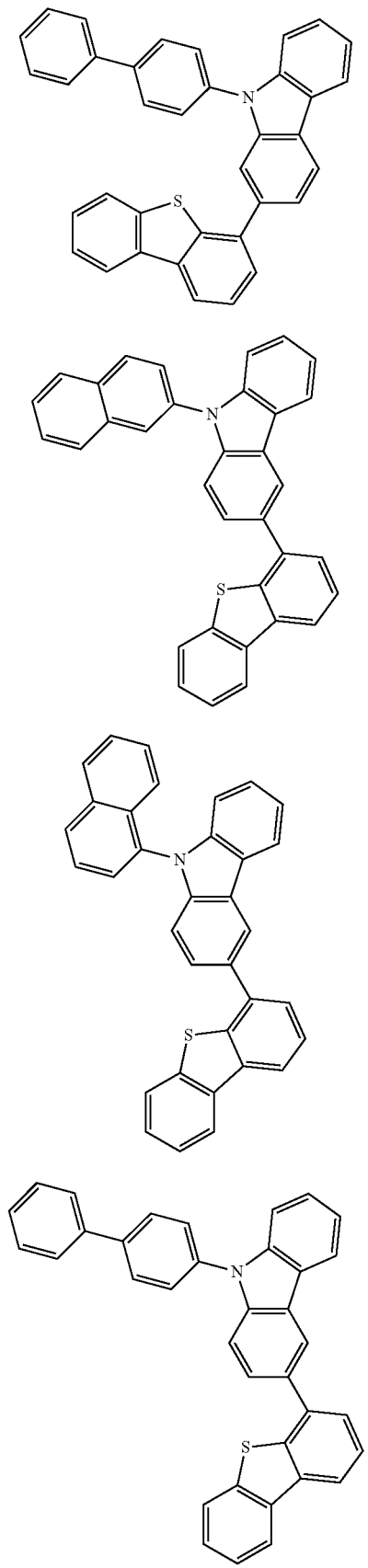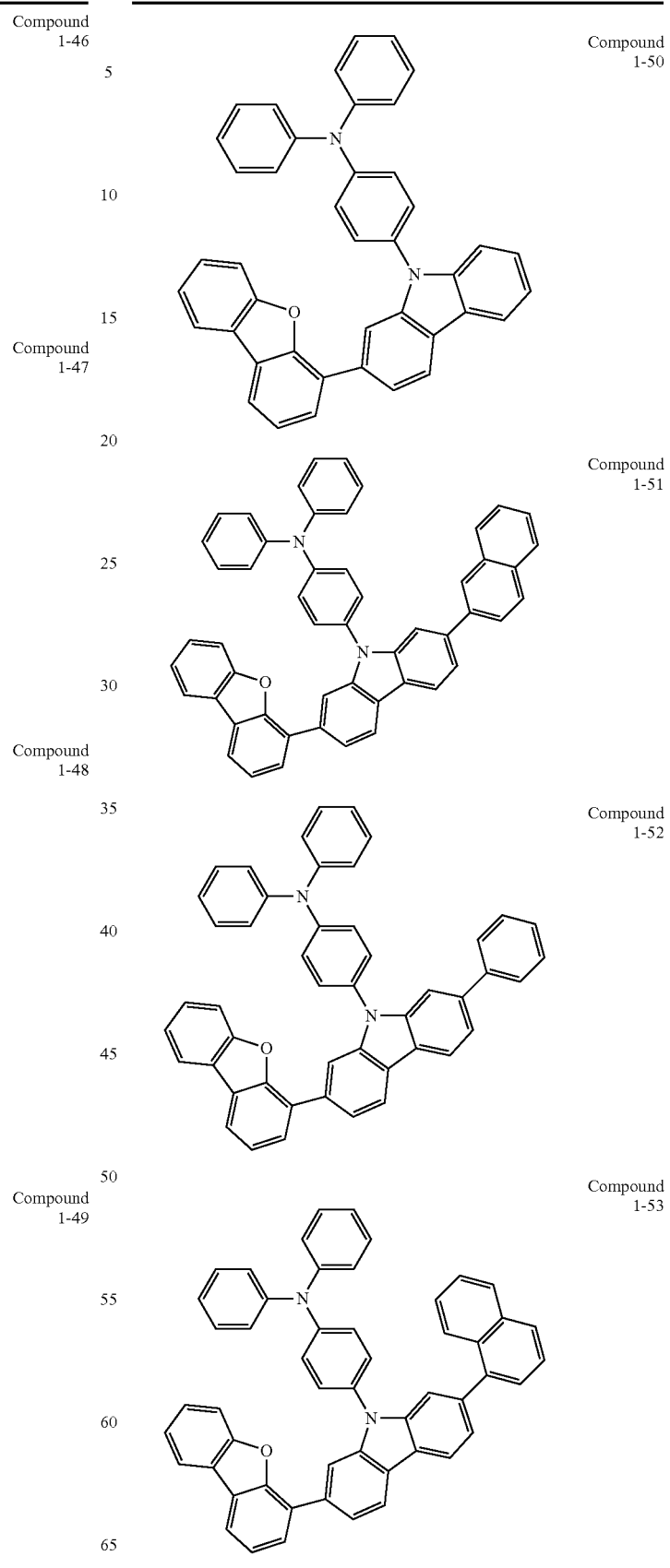

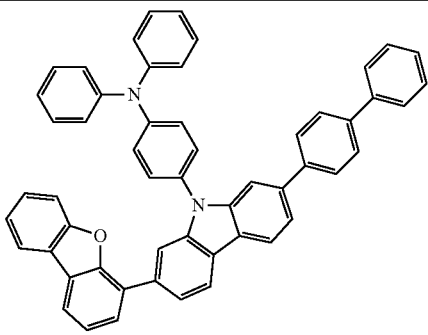

Compound 1-54

One of the typical synthetic routes to synthesize the exemplary compounds represented by Formula (1) is given below, following the conditions cited elsewhere in the literature for Suzuki coupling and Hartwig amination.

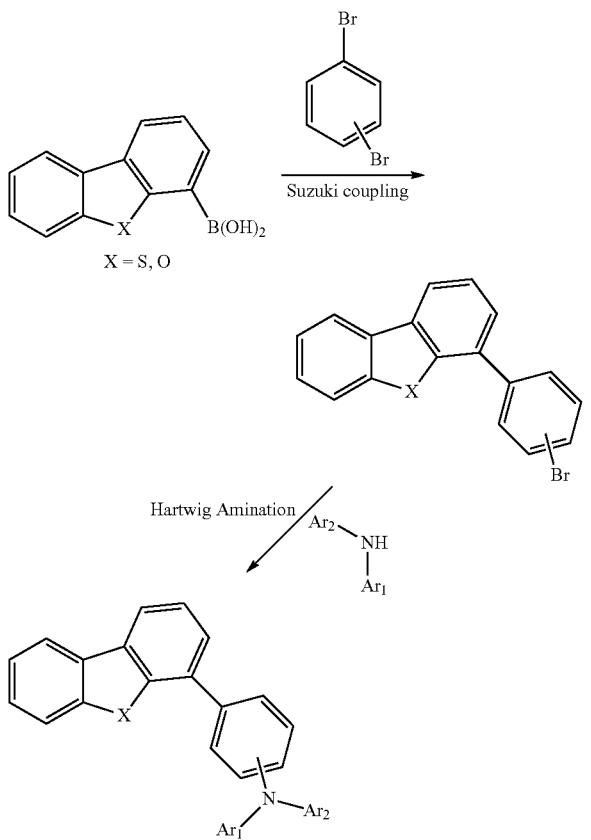

The OLED of the present invention comprises a substrate; an anode formed on the substrate; a cathode; and at least one emitting layer formed between the anode and the cathode, wherein the emitting layer includes a phosphorescent dopant and the above heterocyclic compounds as host material.

The OLED of the present invention further comprises at least one hole auxiliary layer formed between the anode and the emitting layer, and the at least one hole auxiliary layer is selected from the group consisting of a hole injection layer and a hole transport layer. For example, the OLED of the present invention further comprises a hole injection layer and/or a hole transport layer.

In one embodiment of the OLED of the present invention, wherein the at least one hole auxiliary layer contains the above heterocyclic compounds.

The OLED of the present invention further comprises at least one electron auxiliary layer formed between the emitting layer and the cathode, and the at least one electron auxiliary layer is selected from the group consisting of an electron transport layer and an electron injection layer. For example, the OLED of the present invention further comprises an electron transport layer and/or an electron injection layer.

In one embodiment of the OLED of the present invention, the at least one electron auxiliary layer contains the above heterocyclic compounds.

The OLED of the present invention can further comprises an exciton blocking layer formed between the anode and the emitting layer or between the emitting layer and the cathode. For example, the exciton blocking layer is formed between the hole auxiliary layer such as hole injection layer and hole transport layer, and the emitting layer. For another example, the exciton blocking layer is formed between the electron auxiliary layer such as electron transport layer and electron injection layer, and the emitting layer.

In one embodiment of the OLED of the present invention, the exciton blocking layer contains the above heterocyclic compounds.

Phosphorescent dopants to be used in the emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in the present invention.

The content of the phosphorescent dopant used in the emitting layer is preferably in the range of 3 wt % to 15 wt %.

PREFERRED EMBODIMENTS OF THE INVENTION

The structure of the organic electroluminescent device of the present invention will be explained with reference to the drawing, but not limited thereto.

FIG. 1 is a schematic view showing an organic electroluminescent device according to an embodiment of the present invention. An organic electroluminescent device 100 includes a substrate 110, an anode 120, a hole injection layer 130, a hole transport layer 140, an emitting layer 150, an electron transport layer 160, an electron injection layer 170, and a cathode 180. The organic electroluminescent device 100 may be fabricated by depositing the layers described in order.

Figure 2:
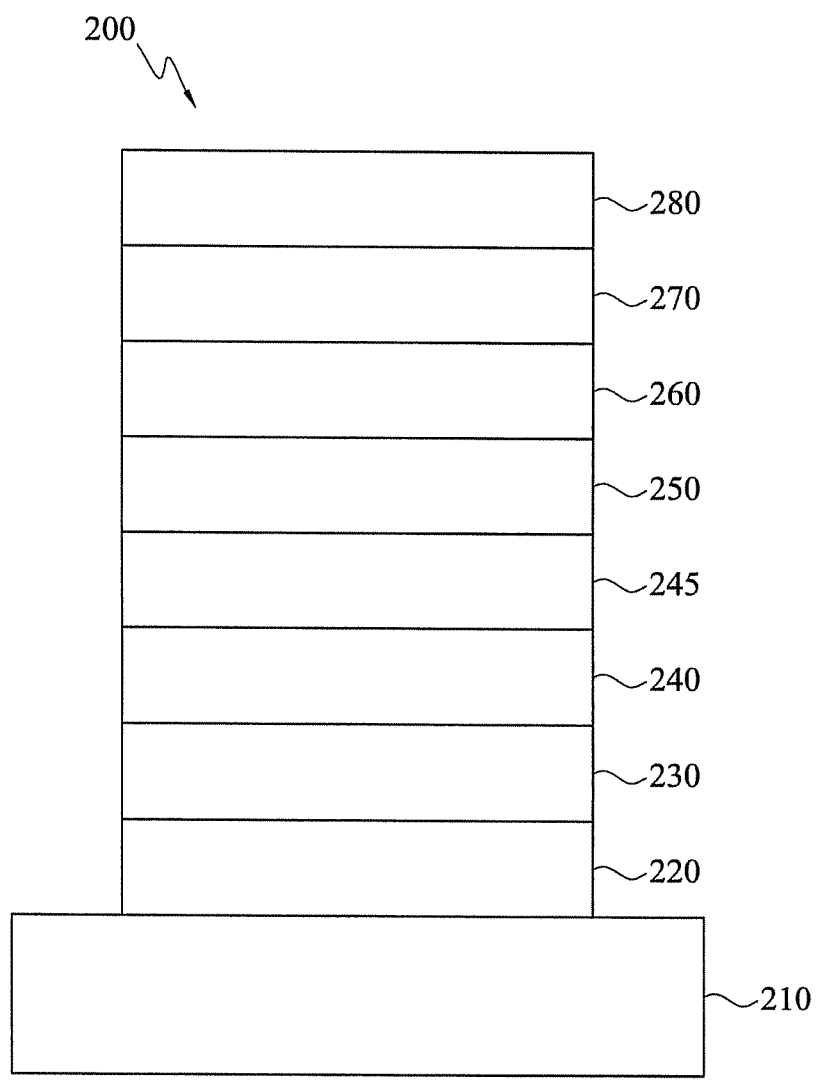
FIG. 2 is a cross-sectional view illustrating another example of an organic electroluminescent device according to another embodiment of the present invention.

FIG. 2 is a schematic view showing an organic electroluminescent device according to another embodiment of the present invention. An organic electroluminescent device 200 includes a substrate 210, an anode 220, a hole injection layer 230, a hole transport layer 240, an exciton blocking layer 245, a emitting layer 250, an electron transport layer 260, an electron injection layer 270, and a cathode 280.

Figure 3:
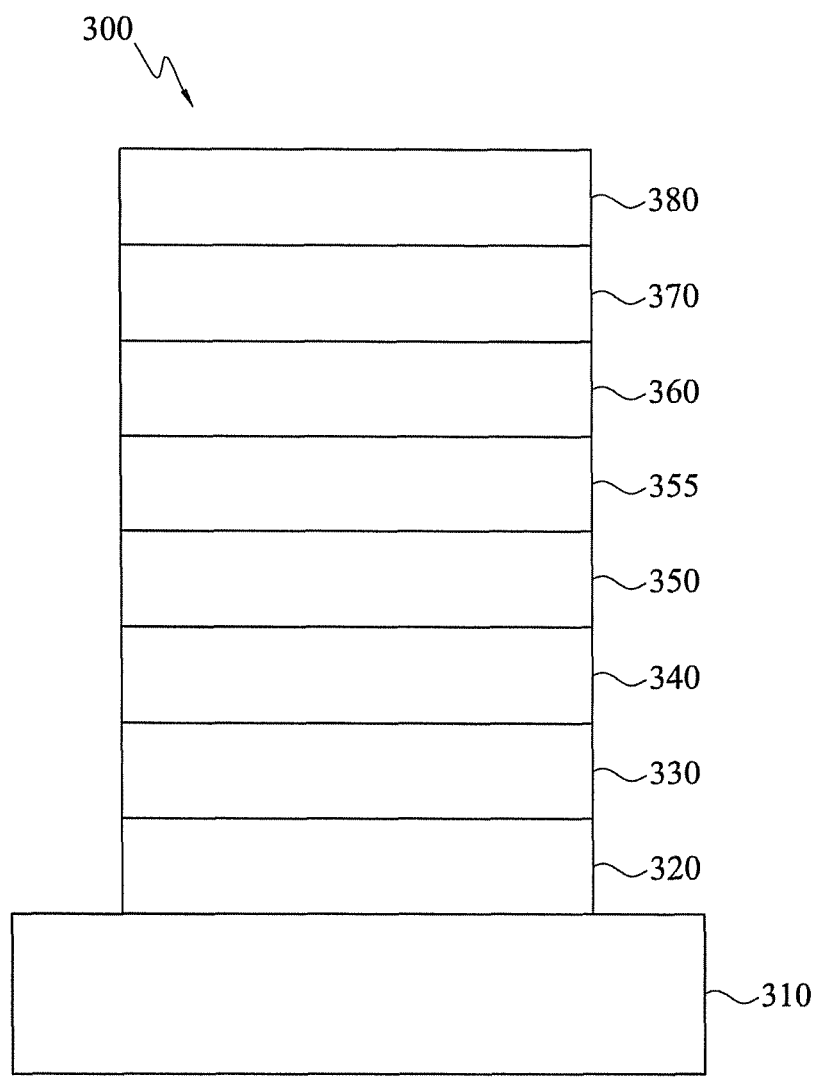
FIG. 3 is a cross-sectional view illustrating yet another example of an organic electroluminescent device according to another embodiment of the present invention.

FIG. 3 is a schematic view showing an organic electroluminescent device according to another embodiment of the present invention. An organic electroluminescent device 300 includes a substrate 310, an anode 320, a hole injection layer 330, a hole transport layer 340, a emitting layer 350, an exciton blocking layer 355, an electron transport layer 360, an electron injection layer 370, and a cathode 380.

It is possible to fabricate an organic electroluminescent device with a structure that is the reverse of the one shown in FIGS. 1-3. In this case of the reverse structure, a layer or layers may be added or omitted as needed.

Materials used in the hole injection layer, the hole transport layer, the exciton blocking layer, the hole blocking layer, the emitting layer, the electron injection layer may be selected from those reported in the literature cited elsewhere.

In addition, U.S. Pat. No. 5,844,363, which is incorporated by reference in its entirety, discloses a flexible and transparent substrate-anode combination. An example of a p-doped hole transport layer is m-MTDATA doped with $F_4$-TCNQ at a molar ratio of 50:1, as disclosed in US Patent Application Publication No. 20030230980, which is incorporated by reference in its entirety. An example of an n-doped electron transport layer is 4,7-di(phenyl)-1,10-phenanthroline (BPhen) doped with Li at a molar ratio of 1:1, as disclosed in US Patent Application Publication No. 20030230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in U.S. Pat. No. 6,097,147 and US Patent Application Publication No. 20030230980, which are incorporated by reference in their entireties. Examples of injection layers are provided in US Patent Application Publication No. 20040174116, which is incorporated by reference in its entirety. A description of protective layers may be found in US Patent Application Publication No. 20040174116, which is incorporated by reference in its entirety.

Structures and materials not specifically described may also be used, such as OLEDs comprised of polymeric materials (PLEDs) such as disclosed in U.S. Pat. No. 5,247,190, which is incorporated by reference in its entirety. Further, OLEDs having a single organic layer may be used. OLEDs may be stacked as described in U.S. Pat. No. 5,707,745, which is incorporated by reference in its entirety.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with deposition methods such as ink-jet and OVJD. Certainly, other methods may be used. The materials to be deposited may be modified to make them compatible with a particular deposition method.

An organic electroluminescent device of the present invention is applicable to a single device, a device with its structure arranged in array, or a device having the anode and the cathode arranged in an X-Y matrix. The present invention significantly improves luminous efficiency and driving stability of an organic electroluminescent device over the conventional devices, when used in combination of phosphorescent dopants in the emitting layer, and furthermore the organic electroluminescent device of the present invention can perform better when applied to full-color or multicolor panels.

EXAMPLES

The present invention will be described in more detail below with reference to the examples; however, it will not be limited to these examples and it can be reduced to practice in various modes unless such practice exceeds the substance of the present invention.

Synthesis Example 1

A mixture of dibenzothiophene-4-boronic acid (10 g), 1,4-Dibromobenzene (9.4 g), tetrakis(triphenylphosphine) palladium (2.42 g), toluene (120 mL), ethanol (16 Ll), water (46 mL) and potassium carbonate (14.44 g) were added together, and stirred at 80° C. for 5 hr. The reaction was monitored by thin layer chromatography; After the completion of the reaction, the reaction mixture was quenched with water (100 mL) and extracted using ethyl acetate (100 mL). The organic layer was extracted with water (3×30 ml) and dried over anhydrous sodium sulfate. The collected ethyl acetate layer was passed through a celite column chromatography for further purification. Subsequently ethyl acetate layer was evaporated to dryness in a rotary evaporator under vacuum to yield 4-(4'-bromophenyl)dibenzothiophene in 13.52 g. A mixture of 4-(4'-bromophenyl)dibenzothiophene (10 g), bis(4-biphenyl)amine (13.08 g), Bis(dibenzylideneacetone)palladium(0) (0.152 g), sodium-t-butoxide (6.52 g), toluene (125 ml), tri(tert-butyl)phosphine (0.274 g), were added together and refluxed under nitrogen atmosphere. The reaction was monitored by thin layer chromatography. After the completion of the reaction, the reaction mixture was quenched with water (50 ml) and extracted using ethyl acetate (100 ml). The organic layer was extracted with water (3×30 ml) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated by adding 200 mL methanol, filtered and dried under vacuum. Compound 1-1 was obtained as a yellow colored solid in 10.38 g (44%) with hplc purity more than 99%. Compound 1-1 showed a melting point of 278.3° C. and a glass transition temperature of 102.9° C.

$^1$H NMR (CDCl3, δ): 8.16-8.11 (m, 2H); 7.79-7.77 (m, 1H); 7.58-7.39 (m, 18H); 7.33-7.22 (m, 8H).

Synthesis Example 2

In a 250 mL flask, a mixture of 4-(4'-bromophenyl) dibenzothiophene (10 g), N-phenylnaphthalen-2-amine (7.75 g), bis(dibenzylideneacetone)palladium(0) (0.59 g), sodium-t-butoxide (6.5 g), toluene (150 ml), tri-(tert-butyl) phosphine (0.55 g) were added together and refluxed under nitrogen atmosphere. The reaction was monitored by thin layer chromatography. After the completion of the reaction, the reaction mixture was quenched with water (50 mL) and extracted using ethyl acetate (70 mL). The organic layer was extracted with water (3×50 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated into methanol (100 ml), filtered and dried under vacuum. Compound 1-3 was obtained as a yellow colored solid in 7 g (49%) with a HPLC purity more than 99%.
Compound 1-3 showed a melting point of 202.21° C. and a glass transition temperature of 82.08° C.
$^1$H NMR (CDCl3, δ): 8.30-8.17 (m, 1H); 8.16-8.10 (in, 1H); 7.88-7.83 (m, 1H); 7.82-7.76 (m 2H); 7.68-7.63 (m, 3H); 7.58-7.30 (m, 9H); 7.29-7.22 (m, 5H); 7.14-7.08 (m, 1H).

Synthesis Example 3

A mixture of 4-dibenzofuranboronic acid (13.3 g), 1,4-Dibromobenzene (10 g), tetrakis(triphenylphosphine)palladium (3.02 g), toluene (158 mL), ethanol (65 mL), water (65 ml) and potassium carbonate (21.69 g) were added together, and stirred at 80° C. for 5 hr. The reaction was monitored by thin layer chromatography. After the completion of the reaction, the reaction mixture was quenched with water (100 mL) and extracted using ethyl acetate (100 mL). The organic layer was extracted with water (3×30 ml) and dried over anhydrous sodium sulfate. The collected ethyl acetate layer was passed through a celite column chromatography for further purification. Subsequently ethyl acetate layer was evaporated to dryness in a rotary evaporator under vacuum to yield 4-(4'-bromophenyl)dibenzofuran in 13.7 g.
In a 500 mL flask, a mixture of 4-(4'-bromophenyl)dibenzofuran (10 g), bis(4-biphenyl)amine (12.7 g), bis(dibenzylideneacetone)palladium(0) (0.62 g), Sodium-t-butoxide (6.9 g), xylene (150 mL), tri(tert-butyl)phosphine (0.58 g) were added together and refluxed under nitrogen atmosphere. The reaction was monitored by thin layer chromatography; after the completion of the reaction, the reaction mixture was quenched with water (50 mL) and extracted using ethyl acetate (70 mL). The organic layer was extracted with water (3×50 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated into methanol (100 ml), filtered and dried under vacuum. Compound 1-7 was obtained as a light-yellow colored solid in 7.67 g (44%) with a HPLC purity more than 99%.
Compound 1-7 showed a glass transition temperature of 96.57° C.
$^1$H NMR (CDCl3, δ): 8.00 (d, 1H); 7.98-7.87 (m, 3H); 7.63-7.53 (m, 10H); 7.49-7.38 (m, 15H).

Synthesis Example 4

In a 500 mL flask, a mixture of 4-(4'-bromophenyl)dibenzofuran (4.2 g), N-(4-biphenyl)-(9,9-dimethylfluoren-2-yl)amine (5 g), bis(dibenzylideneacetone)palladium(0) (0.24 g), sodium-t-butoxide (2.65 g), toluene (75 mL), tri(tert-butyl)phosphine (0.22 g) were added together and refluxed under nitrogen atmosphere. After the completion of the reaction, the reaction mixture was quenched with water (50 mL) and extracted using ethyl acetate (70 mL). The organic layer was extracted with water (3×50 mL) and dried over anhydrous sodium sulfate. The collected ethyl acetate layer was passed through a celite column chromatography for further purification. Subsequently ethyl acetate layer was evaporated to dryness in a rotary evaporator under vacuum. Compound 1-13 was obtained as a yellow colored solid in 3.45 g (44%) with a HPLC purity more than 99%.
Compound 1-13 showed a glass transition temperature of 110.5° C.
$^1$H NMR (CDCl3, δ): 8.01-7.99 (d, 1H); 7.92-7.88 (m, 3H); 7.69-7.55 (m, 11H); 7.49-7.26 (m, 17H); 7.20-7.18 (dd, 1H).

Synthesis Example 5

A mixture of 4-Dibenzofuranboronic acid (13.3 g), 1,3-dibromobenzene (10 g), tetrakis(triphenylphosphine)palladium (3.02 g), toluene (158 mL), ethanol (65 mL), water (65 mL) and potassium carbonate (21.69 g) were added together, and stirred at 80° C. for 5 hr. The reaction was monitored by thin layer chromatography. After the completion of the reaction, the reaction mixture was quenched with water (100 mL) and extracted using ethyl acetate (100 mL). The organic layer was extracted with water (3×30 mL) and dried over anhydrous sodium sulfate. The collected ethyl acetate layer was passed through a celite column chromatography for further purification. Subsequently ethyl acetate layer was evaporated to dryness in a rotary evaporator under vacuum to yield 4-(3'-bromophenyl)dibenzofuran in 13.7 g.
A mixture of 4-(3'-bromophenyl)dibenzofuran (7.4 g), N-(4-biphenyl)-(9,9-dimethylfluoren-2-yl)amine (10 g), Bis(dibenzylideneacetone)palladium(0) (0.46 g), sodium-t-butoxide (5.1 g), toluene (110 mL), tri(tert-butyl)phosphine (0.43 g), were added together and refluxed under nitrogen atmosphere. The reaction was monitored by thin layer chromatography. After the completion of the reaction, the reaction mixture was quenched with water (50 mL) and extracted using ethyl acetate (70 mL). The organic layer was extracted with water (3×50 mL) and dried over anhydrous sodium sulfate. The collected ethyl acetate layer was passed through a celite column chromatography for further purification. Subsequently ethyl acetate layer was evaporated to dryness in a rotary evaporator under vacuum. Compound 1-17 was obtained as a yellow colored solid in 6.12 g (44%) with a HPLC purity more than 99%.
Compound 1-17 showed a glass transition temperature of 103.11° C.
$^1$H NMR (CDCl3, δ): 8.09-7.93 (d, 1H); 7.92-7.89 (d, 1H); 7.73-7.72 (t, 1H); 7.71-7.60 (m, 6H); 7.57-7.30 (m, 22H); 7.29-7.2 (d, d, 2H).

Synthesis Example 6

A mixture of dibenzo[b,d]thiophen-4-ylboronic acid (10 g, 38.4 mmol), 1,3-Dibromobenzene (9.5 g, 40.33 mmol), Tetrakis(triphenylphosphine)palladium (2.3 g, 2.01 mmol), toluene (130 ml), ethanol (17 ml), H$_2$O (45 ml) and Potassium carbonate (13.9 g, 100 mmol) were added together, and stirred at 80° C. for 5 h. The reaction was monitored by thin layer chromatography. After the completion of the reaction, the reaction mixture was quenched with water (100 mL) and extracted using ethyl acetate (100 mL). The organic layer was extracted with water (3×30 mL) and dried over anhydrous sodium sulfate. The collected ethyl acetate layer was passed through a celite column chromatography for further purification. Subsequently ethylacetate layer was evaporated to dryness in a rotary evaporator under vacuum to yield 4-(3-bromophenyl)dibenzo[b,d]thiophene (8.2 g).
A mixture of 4-(3-bromophenyl)dibenzo[b,d]thiophene (8.2 g) (3.5 g, 10.31 mmol), Bis(4-biphenyl)amine (3.48 g, 10.83 mmol), Bis(dibenzylideneacetone)palladium(0) (0.19 g, 0.32 mmol), Sodium-t-butoxide 2 g, 21.65 mmol), xylene (40 ml), Tri-tert-butylphosphine (0.17 g, 0.86 mmole) were added together and refluxed under nitrogen atmosphere. The reaction was monitored by thin layer chromatography. After the completion of the reaction, the reaction mixture was quenched with water (30 mL) and extracted using ethyl acetate (50 mL). The organic layer was extracted with water (3×30 mL) and dried over anhydrous sodium sulfate. The collected ethyl acetate layer was passed through a celite column chromatography for further purification. Subsequently ethyl acetate layer was evaporated to dryness in a rotary evaporator under vacuum. Compound 1-21 was obtained as a yellow colored solid in 3.0 g (50%) with a HPLC purity more than 99%.

Compound 1-21 showed a melting point of 191.22° C. and a glass transition temperature of 93.21° C.

$^1$H NMR (CDCl3, δ): 8.18-8.10 (m, 2H); 7.82-7.78 (m, 1H); 7.62-7.49 (m, 6H); 7.48-7.38 (m, 11H); 7.34-7.22 (m, 9H).

Synthesis Example 7

In a 250 mL flask, a mixture of 4-(3'-bromophenyl) dibenzothiophene (5 g), N-(4-biphenyl)-(9,9-dimethylfluoren-2-yl)amine (6.39 g), bis(dibenzylidene acetone)palladium(0) (0.29 g), Sodium-t-butoxide (3.27 g), toluene (95 mL), Tri-(tert-butyl)phosphine (0.28 g) were added together and refluxed under nitrogen atmosphere. The reaction was monitored by thin layer chromatography. After the completion of the reaction, the reaction mixture was quenched with water (50 mL) and extracted using ethyl acetate (70 mL). The organic layer was extracted with water (3×50 mL) and dried over anhydrous sodium sulfate. The collected ethyl acetate layer was passed through a celite column chromatography for further purification. Subsequently ethyl acetate layer was evaporated to dryness in a rotary evaporator under vacuum. Compound 1-29 was obtained as a yellow colored solid in 3.0 g (32%) with a HPLC purity more than 99%.

Compound 1-29 showed a melting point of 202.82° C. and a glass transition temperature of 107.65° C.

$^1$H NMR (CDCl3, δ): 7.77-7.43 (m, 1H); 7.68-7.62 (m, 3H); 7.62-7.58 (m, 3H); 7.55-7.47 (m, 5H); 7.46-7.23 (m, 20H); 7.20-7.16 (m, 1H).

Synthesis Example 8

A mixture of 4-(3'-bromophenyl)dibenzofuran (2.7 g), bis(4-biphenyl)amine (3.1 g), Bis(dibenzylideneacetone) palladium(0) (0.14 g), Sodium-t-butoxide (1.6 g), xylene (40 ml), Tri-tert-butylphosphine (0.13 g) were added together and refluxed under nitrogen atmosphere. The reaction was monitored by thin layer chromatography. After the completion of the reaction, the reaction mixture was quenched with water (30 mL) and extracted using ethyl acetate (50 mL). The organic layer was extracted with water (3×30 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated by adding 200 ml methanol, filtered and dried under vacuum. Compound 1-32 was obtained as a yellow colored solid in 3 g (63%) with a HPLC purity more than 99%.

Compound 1-32 showed a melting point of 177° C. and a glass transition temperature of 86.8° C.

$^1$H NMR (CDCl3, δ): 7.97-7.94 (d, 1H); 7.92-7.88 (m, 1H); 7.77-7.74 (t, 1H); 7.64-7.54 (m, 10H); 7.51-7.30 (m, 15H); 7.30-7.26 (m, 1H).

Synthesis Example 9

A mixture of 4-(3'-bromophenyl)dibenzo[b,d]thiophene (2.6 g), N1-(naphthalen-1-yl)-N4,N4-diphenylbenzene-1,4-diamine (3.55 g), Bis(dibenzylideneacetone)palladium(0) (0.15 g), Sodium-t-butoxide (1.7 g), toluene (50 mL), Tri-tert-butylphosphine (0.14 g), were added together and refluxed under nitrogen atmosphere. The reaction was monitored by thin layer chromatography. After the completion of the reaction, the reaction mixture was quenched with water (30 mL) and extracted using ethyl acetate (50 mL). The organic layer was extracted with water (3×30 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated by adding 200 ml methanol, filtered and dried under vacuum. Compound 1-40 was obtained as a yellow colored solid in 2 g (40%) with a HPLC purity more than 99%.

Compound 1-40 showed a melting point of 167.01° C. and a glass transition temperature of 99.93° C.

$^1$H NMR (CDCl3, δ): 8.14-8.06 (m, 7H); 7.93-7.90 (d, 3H); 7.71-7.73 (m, 1H); 7.68-7.62 (t, 2H); 7.62-7.58 (m, 2H); 7.55-7.47 (m, 4H); 7.46-7.67 (m, 3H); 7.52-7.39 (m, 19H).

Synthesis Example 10

In a 250 mL flask, a mixture of 4-(4'-bromophenyl) dibenzo[b,d]furan (10 g), Tetrahydrofuran (90 mL) were added together, stirred and cooled to −78° C. under nitrogen atmosphere, injected n-butyllithium solution (18.8 ml, 2.5M in hexanes) at −78° C., and stirred at −78° C. for 2 hr. After 2 h, injected trimethyl borate (16 g) and allowed the reaction to equilibrate to room temperature overnight. The reaction was monitored by thin layer chromatography. After the completion of the reaction, added 2N HCl solution (60 mL) in to the reaction mixture and stirred for 1 h, the reaction mixture was quenched with water (50 mL) and extracted using ethyl acetate (70 mL). The organic layer was extracted with water (3×50 mL) and dried over anhydrous sodium sulfate. Subsequently ethyl acetate layer was evaporated to dryness in a rotary evaporator under vacuum to yield 4-(dibenzofuran-4'-yl)phenyl boronic acid (5 g).

A mixture of 4-(dibenzofuran-4'-yl)phenyl boronic acid (5 g), 2-bromocarbazole (4.7 g), Tetrakis(triphenylphosphine) palladium (1 g), toluene (64 mL), ethanol (7 mL), water (20 mL) and Potassium carbonate (6.6 g) were added together, and stirred under reflux. The reaction was monitored by thin layer chromatography. After the completion of the reaction, the reaction mixture was quenched with water (100 mL) and extracted using ethyl acetate (100 mL). The organic layer was extracted with water (3×30 mL) and dried over anhydrous sodium sulfate. The collected ethyl acetate layer was passed through a celite column chromatography for further purification. Subsequently ethylacetate layer was evaporated to dryness in a rotary evaporator under vacuum to yield Compound 1-44 (1 g, 39%) with a HPLC purity more than 99%.

Compound 1-44 showed a melting point of 246.35° C. and a glass transition temperature of 95.24° C.

$^1$H NMR (CDCl3, δ): 8.34-8.27 (m, 1H); 8.26-8.02 (m, 3H); 7.98-7.88 (m, 2H); 7.86-7.80 (m, 1H); 7.58-7.66 (d, 2H); 7.60-7.40 (m, 7H); 7.38-7.30 (m, 1H); 7.29-7.21 (m, 7H); 7.20-7.10 (m, 1H).

Synthesis Example 11

In a 250 mL flask, a mixture of dibenzo[b,d]thiophen-4-ylboronic acid (5 g, 20.31 mmol), 3-bromocarbazole (4.9 g, 21.33 mmol), Tetrakis(triphenylphosphine)palladium (1.2 g, 1.01 mmol), toluene (60 ml), ethanol (8 ml), H$_2$O (20 ml) and Potassium carbonate (7.4 g 53.33 mmol) were added together, and stirred under reflux for 5 h. The reaction was monitored by thin layer chromatography. After the completion of the reaction, the reaction mixture was quenched with water (30 mL) and extracted using ethyl acetate (50 mL). The organic layer was extracted with water (3×30 mL) and dried over anhydrous sodium sulfate. The collected ethyl acetate layer was passed through a celite column chromatography for further purification. Subsequently ethylacetate layer was evaporated to dryness in a rotary evaporator under vacuum to yield 2-(dibenzo[b,d]thiophen-4-yl)-9H-carbazole (3 g).

A mixture of 2-(dibenzo[b,d]thiophen-4-yl)-9H-carbazole (2 g, 58.72 mmol), 2-bromonaphthalene (1.3 g, 6.29 mmol), Bis(dibenzylideneacetone)palladium(0) (0.1 g, 0.17 mmol), Sodium-t-butoxide (1.1 g, 11.44 mmol), Toluene (30 ml), tri(tert-butyl)phosphine (0.09 g, 0.45 mmole) were added together and refluxed under nitrogen atmosphere. The reaction was monitored by thin layer chromatography. After the completion of the reaction, the reaction mixture was quenched with water (20 mL) and extracted using ethyl acetate (50 mL). The organic layer was extracted with water (3×20 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated by adding 200 ml methanol, filtered and dried under vacuum. Compound 1-47 was obtained as a yellow colored solid in 1 g (36%) with a HPLC purity more than 99%.

Compound 1-47 showed a melting point of 187.51° C. and a glass transition temperature of 101.31° C.

$^1$H NMR (CDCl3, δ): 8.56-8.53 (d, 1H); 8.25-8.14 (m, 3H); 7.13-7.09 (m, 2H); 8.02-7.92 (m, 2H); 7.85-7.79 (m, 2H); 7.76-7.72 (m, 1H); 7.64-7.57 (m, 5H); 7.53-7.42 (m, 4H); 7.37-7.31 (m, 1H)

Synthesis Example 12

In a 150 mL flask, a mixture of 2-(dibenzo[b,d]furan-4-yl)-9H-carbazole (3.5 g), 4-Bromotriphenyl amine (3.7 g), Bis(dibenzylideneacetone)palladium(0) (0.18 g), Sodium-t-butoxide (2 g), toluene (53 mL), tri(tert-butyl)phosphine (0.17 g) were added together and refluxed under nitrogen atmosphere. The reaction was monitored by thin layer chromatography. After the completion of the reaction, the reaction mixture was quenched with water (30 mL) and extracted using ethyl acetate (50 mL). The organic layer was extracted with water (3×30 mL) and dried over anhydrous sodium sulfate. The collected ethyl acetate layer was passed through a celite column chromatography for further purification. Subsequently ethyl acetate layer was evaporated to dryness in a rotary evaporator under vacuum. The residue was further precipitated by adding into methanol, filtered and dried under vacuum. Compound 1-50 was obtained as a yellow colored solid in 3.5 g (57%) with a hplc purity more than 99%.

Compound 1-50 showed a melting point of 283.3° C. and a glass transition temperature of 94.64° C.

$^1$H NMR (CDCl3, δ): 8.29-8.27 (d, 1H); 8.20-8.18 (d, 1H); 8.01-8.00 (m, 2H); 7.95-7.94 (m, 1H); 7.85-7.83 (d, 1H); 7.71-7.69 (m, 1H); 7:55-7.54 (d, 1H); 7.50-7.43 (m, 7H); 7.39-7.36 (t, 1H); 7.31-7.20 (m, 10H); 7.08-7.07 (t, 2H).

Green Electrophosphorescent Devices

Example 1 (Fabrication of Organic Electroluminescent Device)

Prior to use, the substrate was degreased with solvents and cleaned in UV ozone before it was loaded into the evaporation system. The substrate was then transferred into a vacuum deposition chamber for deposition of all other layers on top of the substrate. The following layers were deposited in the following sequence, as shown in FIG. 1, by evaporation from a heated boat under a vacuum of approximately 10$^{-6}$ Torr:

a) a hole injection layer, 20 nm thick, HAT-CN, b) a hole transport layer, 110 nm thick, N,N'-tetra(4-biphenyl)benzidine (HT1);

c) a emitting layer, 30 nm thick, comprising an optimal ratio of PH1 and compound 1-1 doped with 5 wt % GD by volume;

(PH1 is an electron-rich phosphorescent host from eRay optoelectronics Tech Co. Ltd, Taiwan)

d) an electron transport layer, 30 nm thick, ET doped with Lithium quinolate (Liq) in 1:1 ratio;

f) an electron injection layer, 1 nm thick, LiF; and g) a cathode: approximately 150 nm thick, including Al.

Device structure may be denoted as: ITO/HAT-CN (30 nm)/HT1 (110 nm)/PH1:compound 1-1:5% GD (30 nm)/ET:Liq (30 nm)/LiF (1 nm)/Al (150 nm).

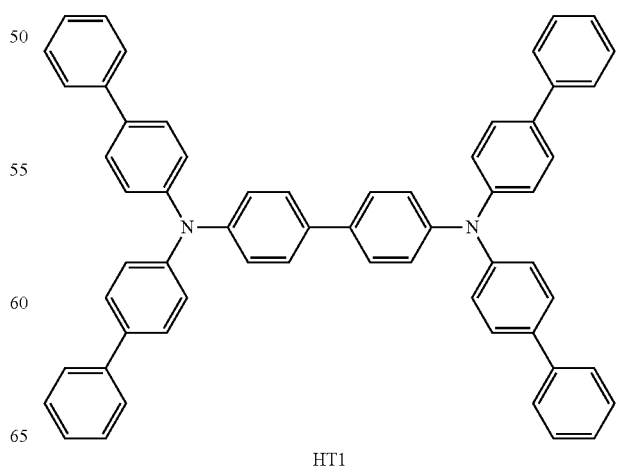

HT1

-continued

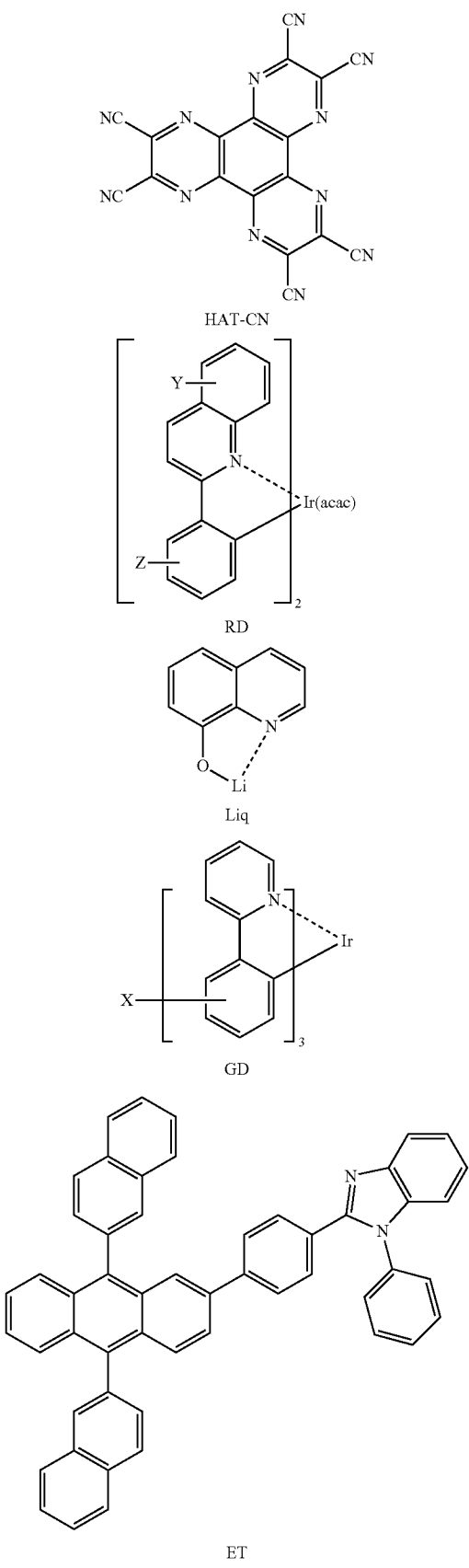

After the deposition of these layers, the device was transferred from the deposition chamber into a dry box for encapsulation, and were subsequently encapsulated using an UV-curable epoxy, and a glass lid containing a moisture getter. The organic EL has an emission area of 3 mm$^2$. The OLED thus obtained was connected to an outside power source and, upon application of direct current voltage, emission of light with the characteristics shown in Table 1 were confirmed.

The EL characteristics of all the fabricated devices were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature. The color was reported using Commission Internationale de l'Eclairage (CIE) coordinates.

Examples 2-7 & Comparative Example 1

Green phosphorescent OLED devices were fabricated similar to the layer structure as example 1 except that suitable compounds as listed in Table 1, were replaced for compound 1-1 in the emitting layer.

Red Electrophosphorescent Devices

Example 8 (Fabrication of OLED)

Red electrophosphorescent devices were fabricated similar to the layer structure as example 1 except that a red phosphorescent dopant was used in the emitting layer. Device structure may be denoted as: ITO/HAT-CN (20 nm)/HT1 (160 nm)/PH1: compound 1-1:3% RD (30 nm)/ET:Liq (30 nm)/LiF (1 nm)/Al (150 nm).

Examples 9-10 & Comparative Example 2

Red phosphorescent OLED devices were fabricated similar to the layer structure as example 1 except that suitable compounds as listed in Table 1, were replaced for compound 1-1 in the emitting layer.

Figure 4:
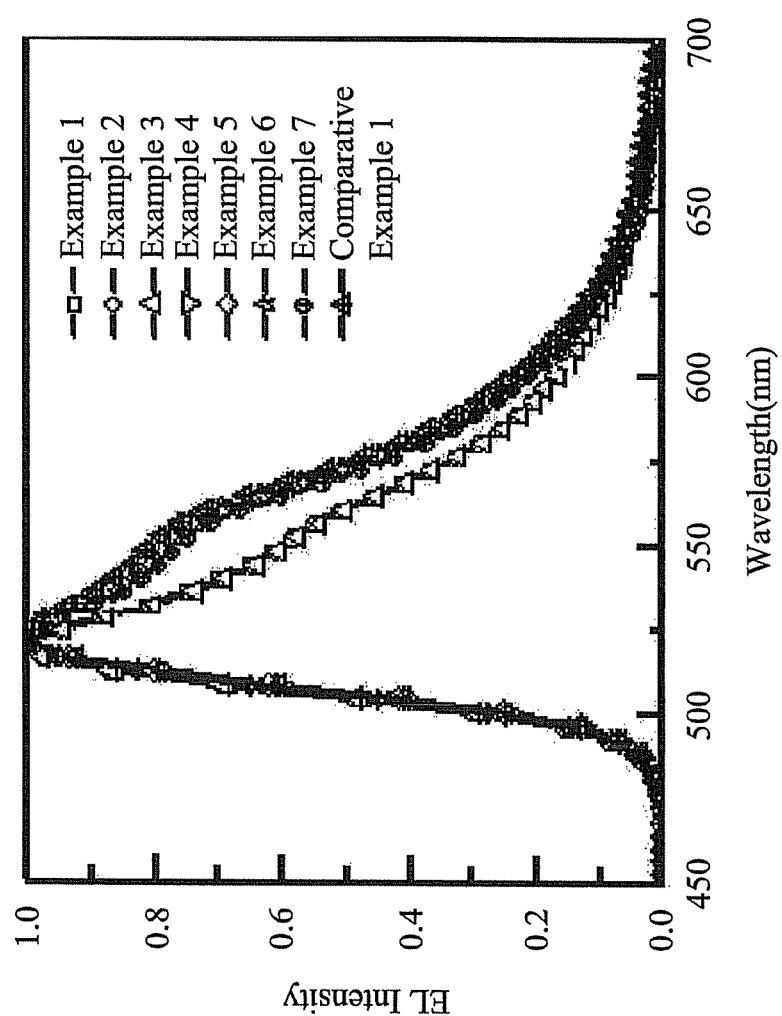
FIG. 4 shows the electroluminescent spectrum of the green electrophosphorescent devices according to the present invention.
Figure 5:
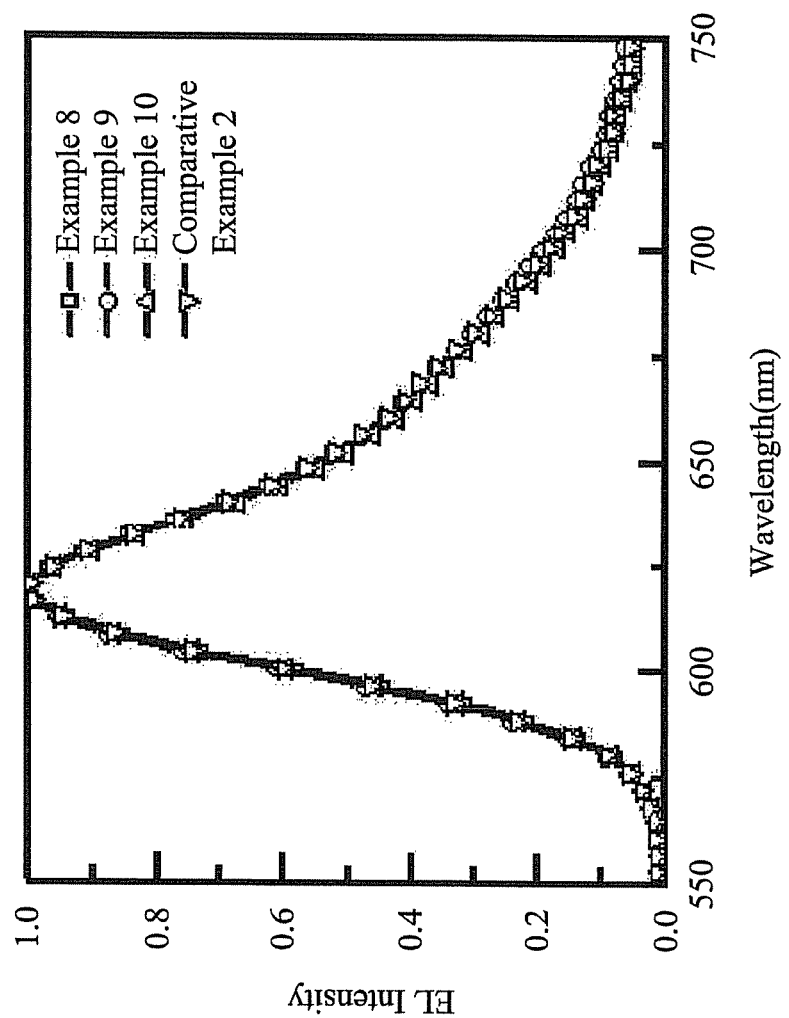
FIG. 5 shows the electroluminescent spectrum of the red electrophosphorescent devices according to the present invention.
Figure 6:
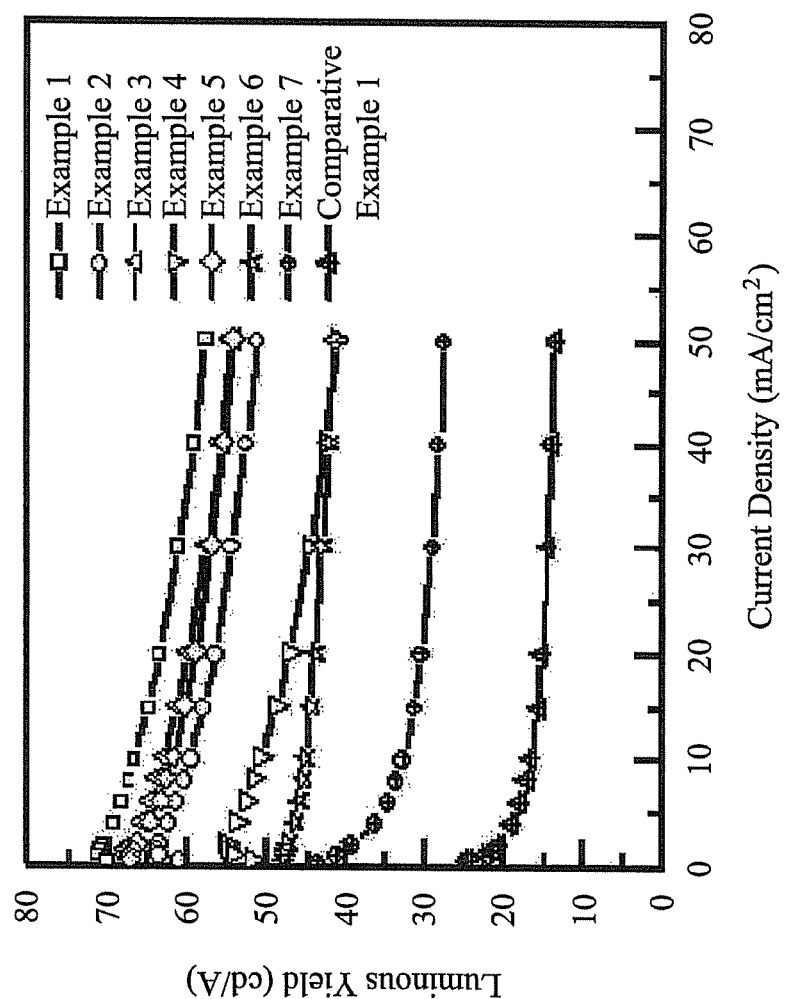
FIG. 6 shows the plot of luminance against current density of the green electrophosphorescent devices according to the present invention.
Figure 7:
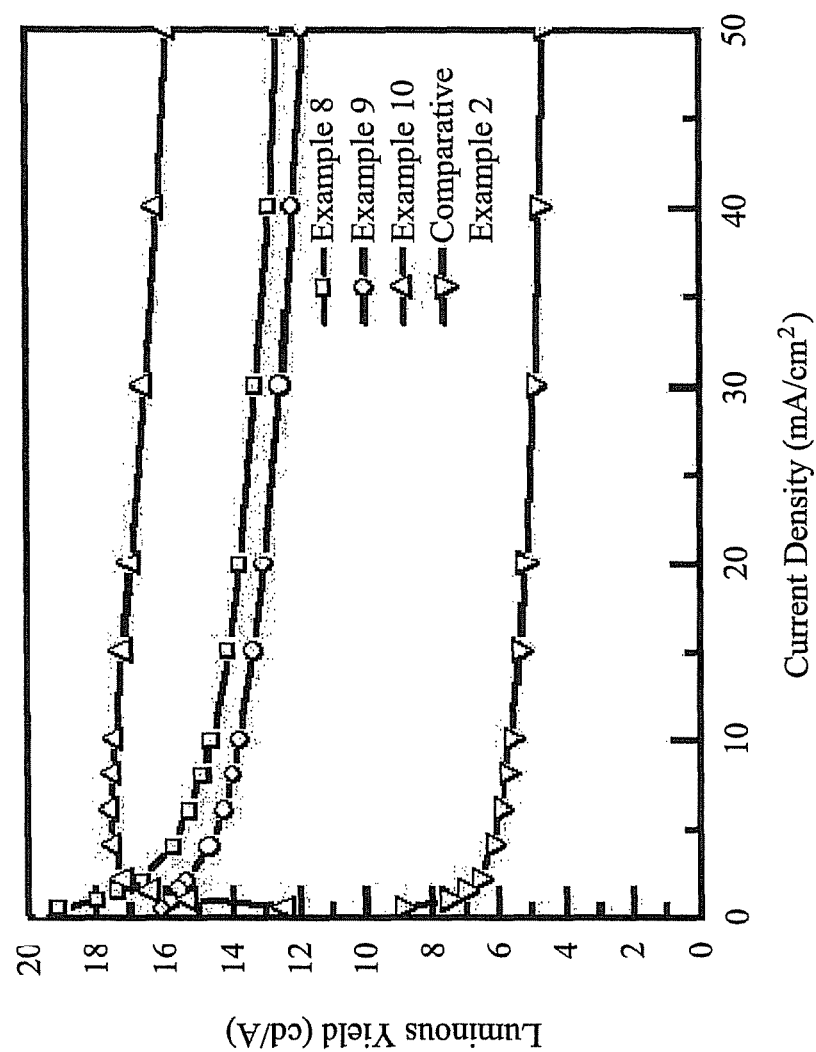
FIG. 7 shows the plot of luminance against current density of the red electrophosphorescent devices according to the present invention.

The peak wavelength of emitted light, maximum luminance efficiency, driving voltage and power efficiency of the OLEDs fabricated in the examples are shown in Table 1. EL spectra of the device examples 1-10 and comparative examples 1 and 2 are shown in FIGS. 4 and 5 and a plot of voltage versus luminance is shown in FIGS. 6 and 7.

TABLE 1

| Devices | Compound of invention used in the emitting layer | Driving voltage (V) | Peak Wavelength (nm) | Emission color | Max. luminance efficiency (cd/A) @ 10 mA/cm$^2$ |
| --- | --- | --- | --- | --- | --- |
| Example 1 | Compound 1-1 | 3.52 | 520 | Green | 66.67 |
| Example 2 | Compound 1-32 | 3.63 | 520 | Green | 59.58 |
| Example 3 | Compound 1-17 | 3.26 | 520 | Green | 62.88 |
| Example 4 | Compound 1-29 | 3.74 | 524 | Green | 50.96 |
| Example 5 | Compound 1-3 | 3.36 | 520 | Green | 61.80 |
| Example 6 | Compound 1-21 | 3.62 | 520 | Green | 45.45 |
| Example 7 | Compound 1-50 | 3.25 | 520 | Green | 32.80 |
| Example 8 | Compound 1-1 | 3.56 | 620 | Red | 14.63 |
| Example 9 | Compound 1-17 | 3.33 | 616 | Red | 13.77 |
| Example 10 | Compound 1-13 | 3.55 | 620 | Red | 17.42 |
| Comparative Example 1 | — | 3.12 | 524 | Green | 16.78 |
| Comparative Example 2 | — | 3.42 | 620 | Red | 5.63 |

The invention shall not be limited by the above described embodiment, method and examples, but by all embodiments and methods within the scope and spirit of the invention as claimed.

INDUSTRIAL APPLICABILITY

As described above in detail, the OLED in which the material for the EL device of the present invention is used is extremely practical because it has high luminous efficiency, high thermal stability, and sufficiently low driving voltage. Therefore, the OLED of the present invention is applicable to flat panel displays, mobile phone displays, light sources utilizing the characteristics of planar light emitters, sign-boards and has a high technical value.

The invention claimed is:

1. A heterocyclic compound represented by the following Formulae:

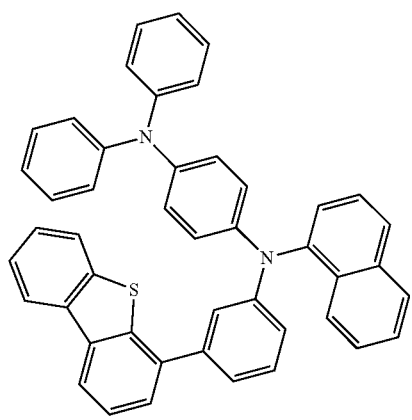

-continued

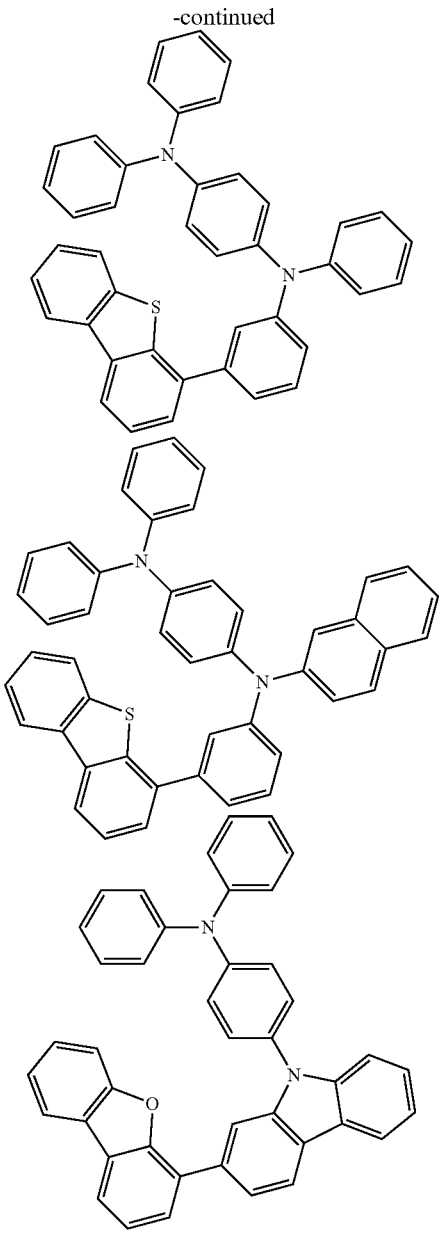

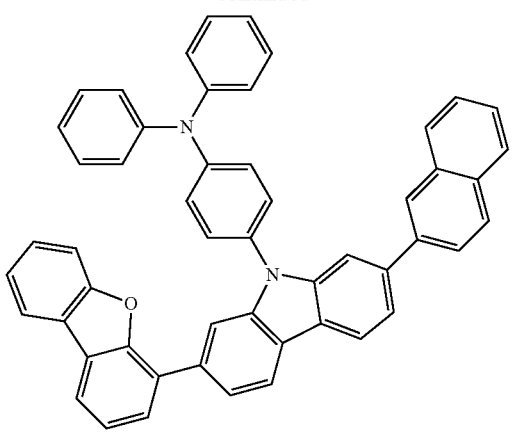

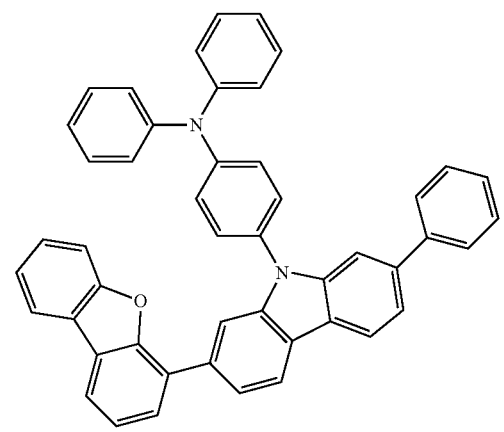

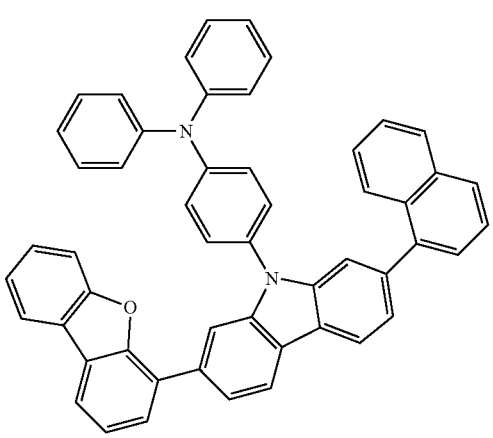

and

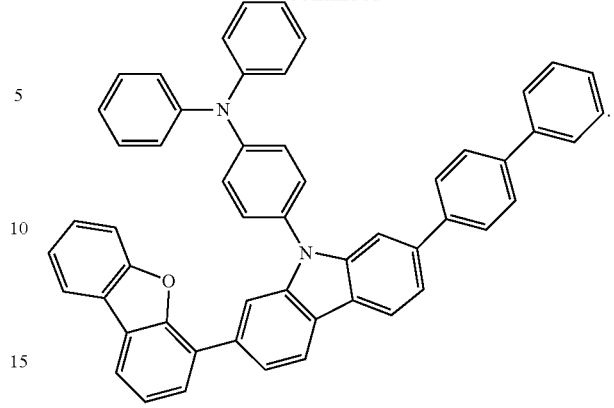

2. An organic electroluminescent device comprising:
a substrate;
an anode formed on the substrate;
a cathode; and
at least one emitting layer formed between the anode and the cathode, wherein the emitting layer includes a phosphorescent dopant and a heterocyclic compound according to claim 1 as host material.

3. The organic electroluminescent device according to claim 2, wherein the phosphorescent dopant is an organic metal complex containing at least one metal selected from the group consisting of ruthenium, rhodium, palladium, silver, rhenium, osmium, iridium, platinum and gold.

4. The organic electroluminescent device according to claim 2, wherein the emitting layer comprises the phosphorescent dopant in a range of 3 wt % to 15 wt %.

5. The organic electroluminescent device according to claim 2, further comprising at least one hole auxiliary layer formed between the anode and the emitting layer, wherein the at least one hole auxiliary layer is selected from the group consisting of a hole injection layer and a hole transport layer.

6. The organic electroluminescent device according to claim 5, wherein the at least one hole auxiliary layer contains the heterocyclic compound according to claim 1.

7. The organic electroluminescent device according to claim 2, further comprising at least one electron auxiliary layer formed between the emitting layer and the cathode, wherein the at least one electron auxiliary layer is selected from the group consisting of an electron transport layer and an electron injection layer.

8. The organic electroluminescent device according to claim 7, wherein the at least one electron auxiliary layer contains the heterocyclic compound according to claim 1.

9. The organic electroluminescent device according to claim 2, further comprising an exciton blocking layer formed between the anode and the emitting layer or between the emitting layer and the cathode.

10. The organic electroluminescent device according to claim 9, wherein the exciton blocking layer contains the heterocyclic compound according to claim 1.

* * * * *